(12) United States Patent
Sullivan et al.

(10) Patent No.: US 12,714,864 B2
(45) Date of Patent: Aug. 25, 2026

(54) RHYTHM SENSING DURING EXTERNAL PACING

(71) Applicant: WEST AFFUM HOLDINGS DAC, Dublin (IE)

(72) Inventors: Joseph L. Sullivan, Kirkland, WA (US); Jaeho Kim, Redmond, WA (US); David P. Finch, Bothell, WA (US)

(73) Assignee: WEST AFFUM HOLDINGS DAC, Dublin (IE)

( * ) Notice: Subject to any disclaimer, the term of this patent is extended or adjusted under 35 U.S.C. 154(b) by 307 days.

(21) Appl. No.: 18/213,783

(22) Filed: Jun. 23, 2023

(65) Prior Publication Data

US 2024/0058613 A1 Feb. 22, 2024

Related U.S. Application Data

(63) Continuation-in-part of application No. 17/561,607, filed on Dec. 23, 2021, now Pat. No. 12,329,973.

(Continued)

(51) Int. Cl.

*A61N 1/365* (2006.01)
*A61B 5/00* (2006.01)

(Continued)

(52) U.S. Cl.

CPC ............ *A61N 1/36585* (2013.01); *A61B 5/33* (2021.01); *A61B 5/363* (2021.01); *A61B 5/4561* (2013.01); *A61B 5/6805* (2013.01); *A61B 5/7405* (2013.01); *A61B 5/746* (2013.01); *A61N 1/3625* (2013.01); *A61N 1/3904* (2017.08); *A61N 1/3925* (2013.01); *A61N 1/3993* (2013.01)

(58) Field of Classification Search

None

See application file for complete search history.

(56) References Cited

U.S. PATENT DOCUMENTS

| | | | |
|---|---|---|---|
| 3,724,355 | A | 4/1973 | Busch et al. |
| 3,724,455 | A | 4/1973 | Unger |

(Continued)

FOREIGN PATENT DOCUMENTS

| | | | |
|---|---|---|---|
| DE | 102005060985 | A1 | 6/2007 |
| EP | 2305110 | A1 | 4/2011 |

(Continued)

OTHER PUBLICATIONS

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.

(Continued)

*Primary Examiner* — Mallika D Fairchild
(74) *Attorney, Agent, or Firm* — Seed Intellectual Property Law Group LLP

(57) ABSTRACT

A wearable medical system (WMS) includes one or more pacing capabilities. The WMS May detect when the patient's heart rhythm starts to deteriorate, but not necessarily in a way that requires Defibrillation. In particular, the WMS may detect bradycardia of one or more types, and then confirm the detection before pacing to treat the detected bradycardia.

20 Claims, 15 Drawing Sheets

COMPONENTS OF SAMPLE WMS

PACING PULSES IN PERIODIC GROUPS WITH PAUSES BETWEEN THE GROUPS

Related U.S. Application Data

(60) Provisional application No. 63/408,833, filed on Sep. 21, 2022, provisional application No. 63/129,887, filed on Dec. 23, 2020.

(51) Int. Cl.
*A61B 5/33* (2021.01)
*A61B 5/363* (2021.01)
*A61N 1/362* (2006.01)
*A61N 1/39* (2006.01)

(56) References Cited

U.S. PATENT DOCUMENTS 4,583,524 A 4/1986 Hutchins
4,619,265 A 10/1986 Morgan et al.
4,666,432 A 5/1987 McNeish et al.
4,698,848 A 10/1987 Buckley
4,928,690 A 5/1990 Heilman et al.
4,955,381 A 9/1990 Way et al.
5,078,134 A 1/1992 Heilman et al.
5,228,449 A 7/1993 Christ et al.
5,348,008 A 9/1994 Born et al.
5,353,793 A 10/1994 Born
RE34,800 E 11/1994 Hutchins
5,394,892 A 3/1995 Kenny
5,405,362 A 4/1995 Kramer et al.
5,429,593 A 7/1995 Matory
5,439,482 A 8/1995 Adams et al.
5,474,574 A 12/1995 Payne et al.
5,618,208 A 4/1997 Crouse et al.
5,662,690 A 9/1997 Cole et al.
5,708,978 A 1/1998 Johnsrud
5,741,306 A 4/1998 Glegyak et al.
5,782,878 A 7/1998 Morgan et al.
5,792,204 A 8/1998 Snell
5,902,249 A 5/1999 Lyster
5,913,685 A 6/1999 Hutchins
5,944,669 A 8/1999 Kaib
6,047,203 A 4/2000 Sackner et al.
6,065,154 A 5/2000 Hulings et al.
6,108,197 A 8/2000 Janik
6,148,233 A 11/2000 Owen et al.
6,201,992 B1 3/2001 Freeman
6,263,238 B1 7/2001 Brewer et al.
6,280,461 B1 8/2001 Glegyak et al.
6,287,328 B1 9/2001 Snyder et al.
6,304,780 B1 10/2001 Owen et al.
6,319,011 B1 11/2001 Motti et al.
6,334,070 B1 12/2001 Nova et al.
6,356,785 B1 3/2002 Snyder
6,427,083 B1 7/2002 Owen et al.
6,437,083 B1 8/2002 Brack et al.
6,450,942 B1 9/2002 Lapanashvili et al.
6,529,875 B1 3/2003 Nakajima
6,546,285 B1 4/2003 Owen et al.
6,671,545 B2 12/2003 Fincke
6,681,003 B2 1/2004 Linder et al.
6,762,917 B1 7/2004 Verbiest et al.
7,065,401 B2 6/2006 Worden
7,099,715 B2 8/2006 Korzinov et al.
7,212,850 B2 5/2007 Prystowsky et al.
7,559,902 B2 7/2009 Ting et al.
7,587,237 B2 9/2009 Korzinov et al.
7,753,759 B2 7/2010 Pintor et al.
7,865,238 B2 1/2011 Brink
7,870,761 B2 1/2011 Valentine et al.
7,907,996 B2 3/2011 Prystowsky et al.
7,941,207 B2 5/2011 Korzinov
7,974,689 B2 7/2011 Volpe et al.
8,135,462 B2 3/2012 Owen et al.
8,140,154 B2 3/2012 Donnelly et al.
8,369,944 B2 2/2013 Macho et al.
8,527,028 B2 9/2013 Kurzweil et al.
8,548,557 B2 10/2013 Garstka et al.
8,560,044 B2 10/2013 Kurzweil et al.
8,615,295 B2 12/2013 Savage et al.
8,644,925 B2 2/2014 Volpe et al.
8,676,313 B2 3/2014 Volpe et al.
8,706,255 B2 4/2014 Phillips et al.
8,742,349 B2 6/2014 Urbon et al.
8,838,236 B2 9/2014 Debardi et al.
8,897,860 B2 11/2014 Volpe et al.
8,904,214 B2 12/2014 Volpe et al.
8,965,500 B2 2/2015 Macho et al.
8,983,597 B2 3/2015 Whiting et al.
9,008,801 B2 4/2015 Kaib et al.
9,084,583 B2 7/2015 Mazar et al.
9,089,685 B2 7/2015 Sullivan et al.
9,119,547 B2 9/2015 Cazares et al.
9,131,901 B2 9/2015 Volpe et al.
9,132,267 B2 9/2015 Kaib
9,265,432 B2 2/2016 Warren et al.
9,320,904 B2 4/2016 Whiting et al.
9,345,898 B2 5/2016 Piha et al.
9,408,548 B2 8/2016 Volpe et al.
9,445,719 B2 9/2016 Libbus et al.
9,454,219 B2 9/2016 Volpe et al.
9,579,020 B2 2/2017 Libbus et al.
9,592,403 B2 3/2017 Sullivan
9,598,799 B2 3/2017 Shoshani et al.
9,604,070 B2 3/2017 Sullivan et al.
9,675,804 B2 6/2017 Whiting et al.
9,724,008 B2 8/2017 Sullivan et al.
9,878,171 B2 1/2018 Kaib
9,895,105 B2 2/2018 Romem
9,901,741 B2 2/2018 Chapman et al.
RE46,926 E 7/2018 Bly et al.
10,016,613 B2 7/2018 Kavounas
10,076,656 B2 9/2018 Dar et al.
10,192,387 B2 1/2019 Brinig et al.
10,307,133 B2 6/2019 Kaib
10,328,266 B2 6/2019 Whiting et al.
10,384,066 B2 8/2019 Whiting et al.
10,463,867 B2 11/2019 Kaib et al.
10,589,110 B2 3/2020 Oskin et al.
10,599,814 B2 3/2020 Landrum et al.
10,898,095 B2 1/2021 Whiting et al.
2002/0181680 A1 12/2002 Linder et al.
2003/0158593 A1 8/2003 Heilman et al.
2004/0193222 A1* 9/2004 Sullivan ............... A61N 1/3625 607/9
2005/0107833 A1 5/2005 Freeman et al.
2005/0107834 A1 5/2005 Freeman et al.
2006/0173499 A1 8/2006 Hampton et al.
2008/0312709 A1 12/2008 Volpe et al.
2009/0005827 A1 1/2009 Weintraub et al.
2010/0007413 A1 1/2010 Herleikson
2010/0298899 A1 11/2010 Donnelly et al.
2011/0022105 A9 1/2011 Owen et al.
2011/0288604 A1 11/2011 Kaib et al.
2011/0288605 A1 11/2011 Kaib et al.
2012/0112903 A1 5/2012 Kaib et al.
2012/0144551 A1 6/2012 Guldalian
2012/0150008 A1 6/2012 Kaib et al.
2012/0158075 A1 6/2012 Kaib et al.
2012/0191476 A1 7/2012 Reid et al.
2012/0265265 A1 10/2012 Razavi et al.
2012/0283794 A1 11/2012 Kaib et al.
2012/0293323 A1 11/2012 Kaib et al.
2012/0302860 A1 11/2012 Volpe et al.
2012/0310315 A1 12/2012 Savage et al.
2013/0085538 A1 4/2013 Volpe et al.
2013/0144355 A1 6/2013 Macho et al.
2013/0231711 A1 9/2013 Kaib
2013/0245388 A1 9/2013 Rafferty et al.
2013/0274565 A1 10/2013 Langer et al.
2013/0317852 A1 11/2013 Worrell et al.
2013/0325078 A1* 12/2013 Whiting ............. A61N 1/36592 607/7
2014/0012144 A1 1/2014 Crone
2014/0025131 A1 1/2014 Sullivan et al.
2014/0046391 A1 2/2014 Cowan et al.
2014/0070957 A1 3/2014 Longinotti-Buitoni et al.

(56) References Cited

U.S. PATENT DOCUMENTS

2014/0163663 A1 6/2014 Poddar et al.
2014/0324112 A1 10/2014 Macho et al.
2014/0378812 A1 12/2014 Saroka et al.
2015/0039053 A1 2/2015 Kaib et al.
2015/0161554 A1 6/2015 Sweeney et al.
2015/0265845 A1* 9/2015 Sullivan ............... A61N 1/3975 607/8
2015/0297135 A1 10/2015 Shoshani et al.
2015/0328472 A1 11/2015 Sullivan et al.
2016/0004831 A1 1/2016 Carlson et al.
2016/0076175 A1 3/2016 Rock et al.
2016/0076176 A1 3/2016 Rock et al.
2016/0082277 A1 3/2016 Foshee, Jr. et al.
2016/0113581 A1 4/2016 Amir et al.
2016/0256104 A1 9/2016 Romem et al.
2016/0283900 A1 9/2016 Johnson et al.
2016/0303371 A1* 10/2016 Whiting ............... A61B 5/6831
2017/0014073 A1 1/2017 Shoshani et al.
2017/0027469 A1 2/2017 Amir et al.
2017/0036066 A1 2/2017 Chahine
2017/0040758 A1 2/2017 Amir et al.
2017/0162840 A1 6/2017 Pendry
2017/0319862 A1 11/2017 Foshee, Jr. et al.
2017/0367591 A1 12/2017 Jorgensen
2018/0116537 A1 5/2018 Sullivan et al.
2018/0117299 A1 5/2018 Gustavson et al.
2018/0184933 A1 7/2018 Sullivan et al.
2018/0185662 A1* 7/2018 Foshee, Jr. ........... A61B 5/6823
2018/0243578 A1 8/2018 Volosin
2018/0344200 A1* 12/2018 Thakur ................ A61B 5/0044
2018/0361165 A1 12/2018 Jaax et al.
2019/0030352 A1 1/2019 Sullivan et al.
2019/0076666 A1 3/2019 Medema
2019/0116896 A1 4/2019 Armour et al.
2019/0262608 A1 8/2019 Whiting et al.
2019/0275335 A1* 9/2019 Volpe ................... A61N 1/3968
2019/0321650 A1 10/2019 Raymond et al.
2020/0197713 A1 6/2020 Clark et al.
2021/0106269 A1 4/2021 Whiting et al.
2021/0330973 A1 10/2021 Whiting et al.

FOREIGN PATENT DOCUMENTS

EP 2854940 A2 4/2015
EP 3380189 B1 10/2018
JP 4320257 B2 8/2009
JP 2014526282 A 10/2014
JP 5963767 B2 8/2016
WO 1998039061 A2 9/1998
WO 2011/146448 A1 11/2011
WO 2012064604 A1 5/2012
WO 2012/151160 A1 11/2012
WO 2015/056262 A1 4/2015

OTHER PUBLICATIONS

LIFECOR LifeVest System Model WCD 3100 Operator's Manual, 2006, PN 20B0040 Rev FI, Zoll Lifecor Corporation, Pittsburgh, PA.
LifeVest Model 4000 Patient Manual, Zoll, 2009, PN 20B0047 Rev B.
Heartstart MRx and XL AED Algorithm—Application Note, Jul. 2001, Edition 2 Philips Healthcare, USA.
The LifeVest Network/Patient Data Management System, Zoll, 2015, 20C0503 Rev A.
Metting Van Rijn, A. C., Peper A., & Grimbergen, C. A., High-Quality Recording of Bioelectric Events Part 1: Interference Reduction, Theory and Practice, Review, Medical & Biological Engineering & Computing, Sep. 1990, pp. 389-397, IFMBE.
Pagan-Carlo, et al., "Encircling Overlapping Multipulse Shock Waveforms for Transthoracic Defibrillation," JACC Journals, Dec. 1998, vol. 32 Issue 7, p. 2065-2071.
Zoll, LifeVest, Proven protection from Sudden Cardiac Death, 2017, Pittsburgh PA, USA, 4 pages.
International Search Report and Written Opinion for PCT Application No. PCT/US2015/051726, dated May 20, 2016, European Patent Office, Rijswijk, (11 pages).

* cited by examiner

SAMPLE COMPONENTS OF WEARABLE MEDICAL SYSTEM (WMS)

SAMPLE COMPONENTS OF EXTERNAL DEFIBRILLATOR AND/OR PACER

COMPONENTS OF SAMPLE WMS

ACTUAL ECG WAVEFORM WITH PACING AND NO NOISE

ACTUAL ECG WAVEFORM WITH PACING AND NOISE

*PACING PULSES IN PERIODIC GROUPS WITH PAUSES BETWEEN THE GROUPS*

*DETECTING QRS COMPLEXES IN ECG SIGNAL PORTIONS DURING THE INTERVALS (IDEALIZED WAVEFORMS)*

RHYTHM SENSING DURING EXTERNAL PACING

CROSS REFERENCE TO RELATED PATENT APPLICATIONS

This patent application claims priority from U.S. Provisional Patent Application Ser. No. 63/408,833, filed on Sep. 21, 2022 and is a continuation-in-part of U.S. patent application Ser. No. 17/561,607, filed Dec. 2, 2021, which claims priority from U.S. provisional patent application Ser. No. 63/129,887, filed on Dec. 23, 2020, both of which are incorporated by reference in their entirety for all purposes.

BACKGROUND

When people suffer from some types of heart arrhythmias, the result may be that blood flow to various parts of the body is reduced. Some arrhythmias may even result in a Sudden Cardiac Arrest (SCA). SCA can lead to death very quickly, e.g. within 10 minutes, unless treated in the interim. Some observers may have thought that SCA is the same as a heart attack, but it is not.

Some people have an increased risk of SCA. Such people include patients who have had a heart attack, or a prior SCA episode. A frequent recommendation for these people is to receive an Implantable Cardioverter Defibrillator (ICD). The ICD is surgically implanted in the chest, and continuously monitors the patient's electrocardiogram (ECG). If certain types of heart arrhythmias are detected, then the ICD delivers an electric shock through the heart.

As a further precaution, people who have been identified to have an increased risk of an SCA are sometimes given a Wearable Cardioverter Defibrillator (WCD) system, to wear until the time that their ICD is implanted. Early versions of such systems were called wearable cardiac defibrillator systems. A WCD system typically includes a harness, vest, belt, or other garment that the patient is to wear. The WCD system further includes electronic components, such as a defibrillator and electrodes, coupled to the harness, vest, or other garment. When the patient wears the WCD system, the electrodes may make good electrical contact with the patient's skin, and therefore can help sense the patient's ECG. If a shockable heart arrhythmia is detected from the ECG, then the defibrillator delivers an appropriate electric shock through the patient's body, and thus through the heart. This may restart the patient's heart, and thus save their life.

WCDs have far harder challenges to overcome, than regular monitor-defibrillators that are carried by trained professionals, or AEDs (Automated External Defibrillators) that may be used by a bystander. In both the scenarios of a monitor-defibrillator and an AED, the patient is typically motionless. A WCD does not necessarily have an operator and, in such situations, it must operate autonomously—make detections, deliver treatments and so on. For detection, a WCD may have far worse challenges due to electrical noise, since the patient may be conscious before SCA, moving, which generates electrical noise, and/or there is no operator to ensure good electrical contacts for the electrodes to suppress the electrical noise.

All subject matter discussed in this Background section of this document, including recognition of challenges, is not necessarily prior art, and may not be presumed to be prior art simply because it is presented in this Background section. Plus, any reference to any prior art in this description is not, and should not be taken as, an acknowledgement or any form of suggestion that such prior art forms parts of the common general knowledge in any art in any country. Along these lines, any recognition of problems in the prior art discussed in this Background section or associated with such subject matter should not be treated as prior art, unless expressly stated to be prior art. Rather, the discussion of any subject matter in this Background section should be treated as part of the approach taken towards the particular problem by the inventors. This approach in and of itself may also be inventive.

BRIEF SUMMARY

The present description gives instances of Wearable Medical Systems (WMSs), storage media that may store programs, and methods, the use of which may help overcome problems and limitations of the prior art.

In embodiments, a WMS includes one or more pacing capabilities. The WMS may detect when the patient's heart rhythm starts to deteriorate, but not necessarily in a way that requires defibrillation. In particular, the WMS may detect bradycardia of one or more types, and then confirm the detection before pacing to treat the detected bradycardia.

In embodiments, a WMS includes one or more pacing capabilities. The WMS may detect when the patient's heart rhythm starts to deteriorate, but not necessarily in a way that requires defibrillation. In particular, the WMS applies the same pacing sequence to treat bradycardia and asystole. Optionally, it also applies this pacing sequence after a defibrillation shock, to treat post-shock bradycardia or perhaps repeating events of asystole.

In embodiments, a WMS includes one or more pacing capabilities. The WMS may detect when the patient's heart rhythm starts to deteriorate, but not necessarily in a way that requires defibrillation. In particular, the WMS may pace the patient and concurrently monitor for arrhythmias. Upon detecting an arrhythmia, the WMS may continue, adjust, or discontinue the pacing.

As such, it will be appreciated that results of embodiments are larger than the sum of their individual parts, and have substantial utility.

These and other features and advantages of the claimed invention will become more readily apparent in view of the embodiments described and illustrated in this specification, namely in this written specification and the associated drawings.

DETAILED DESCRIPTION

As has been mentioned, the present description is about Wearable Medical Systems (WMSs), storage media that may store programs, and methods. Such systems may include a pacer and/or a defibrillator. It they include both, they may also be called Wearable Cardioverter Pacemaker Defibrillator (WPCD) systems. If they include only a defibrillator, they may also be called Wearable Cardioverter Defibrillator (WCD) systems. If they include only a pacer, which is also known as a pacemaker, they may also be called Wearable Pacer (WP) systems. Embodiments are now described in more detail.

A wearable medical system (WMS) according to embodiments may protect an ambulatory patient by electrically restarting their heart if needed. Such a WMS may have a number of components. These components can be provided separately as modules that can be interconnected, or can be combined with other components, and so on.

Figure 1:
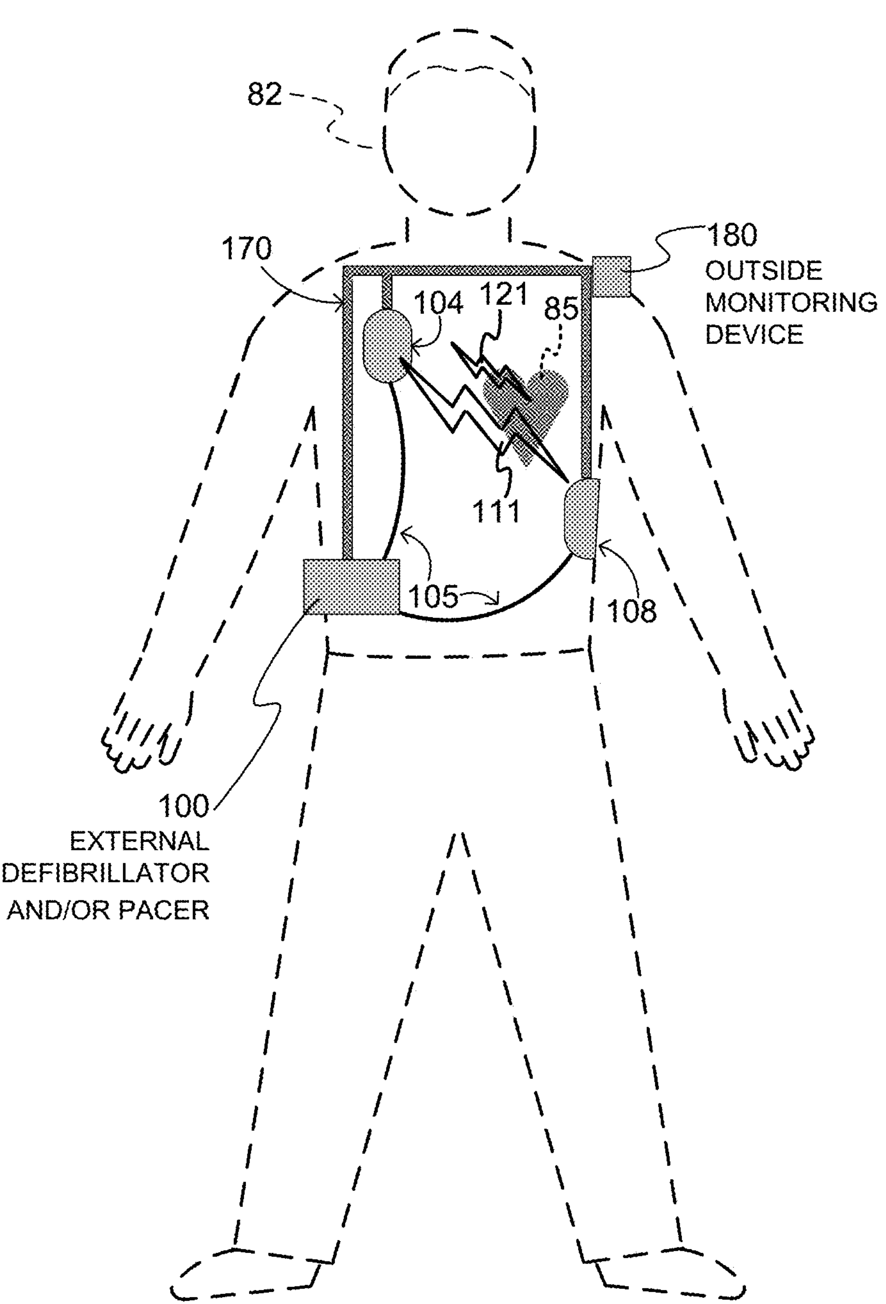
FIG. 1 is a diagram of sample components of a wearable medical system (WMS), which is made according to embodiments.

FIG. 1 depicts a patient 82. The patient 82 may also be referred to as the person 82 and/or wearer 82, since the patient 82 is wearing components of the WMS. The patient 82 is ambulatory, which means that, while wearing the wearable portion of the WMS, the patient 82 can walk around and is not necessarily bed-ridden. However, in accordance with the present disclosure, embodiments of the WMSs described herein (including those described in conjunction with other FIGS.) can be worn by non-ambulatory patients and the WMS embodiments will operate in the substantially the same manner as when worn by ambulatory patients. While the patient 82 may be considered to be also a "user" of the WMS, this definition is not exclusive to the patient 82. For instance, a user of the wearable medical system (WMS) may also be a clinician such as a doctor, nurse, emergency medical technician (EMT) or other similarly tasked individual or group of individuals. In some cases, a user may even be a bystander. The particular context of these and other related terms within this description should be interpreted accordingly.

In some embodiments a WMS is configured to also defibrillate the patient who is wearing the designated parts the WMS. Defibrillating can be by the WMS delivering an electrical charge to the patient's body in the form of an electric shock. This electric shock is also known as a defibrillation shock, and its energy can be more than 100 Joule (J), such as 200 J, 300 J, 360 J and so on. The electric shock can be delivered in one or more pulses.

In particular, FIG. 1 also depicts components of a WMS made according to embodiments. One such component is a support structure 170 that is wearable by the ambulatory patient 82. Accordingly, the support structure 170 can be configured to be worn by the ambulatory patient 82 for at least several hours per day, and also during the night. That, for at least several days, even a few months. It will be understood that the support structure 170 is shown only generically in FIG. 1, and in fact partly conceptually. FIG. 1 is provided merely to illustrate concepts about the support structure 170, and is not to be construed as limiting how the support structure 170 is implemented, or how it is worn.

The support structure 170 can be implemented in many different ways. For example, it can be implemented in a single component or a combination of multiple components. In embodiments, the support structure 170 could include a vest, a half-vest, a garment, etc. In such embodiments such items can be worn similarly to analogous articles of clothing. In embodiments, the support structure 170 could include a harness, one or more belts or straps, etc. In such embodiments, such items can be worn by the patient around the torso, hips, over the shoulder, etc. In embodiments, the support structure 170 can include a container or housing, which can even be waterproof. In such embodiments, the support structure can be worn by being attached to the patient's body by adhesive material, for example as shown and described in U.S. Pat. No. 8,024,037. The support structure 170 can even be implemented as described for the support structure of US Pat. App. No. US2017/0056682, which is incorporated herein by reference. Of course, in such embodiments, the person skilled in the art will recognize that additional components of the WMS can be in the housing of a support structure instead of being attached externally to the support structure, for example as described in the US2017/0056682 document. There can be other examples.

FIG. 1 shows a sample external defibrillator and/or pacer 100. As described in more detail later in this document, some aspects of the external defibrillator and/or pacer 100 include a housing and an energy storage module within the housing. As such, in the context of a WMS, the defibrillator and/or pacer 100 is sometimes called a main electronics module. The energy storage module can be configured to store an electrical charge. Other components can cause at least some of the stored electrical charge to be discharged via electrodes through the patient, so as to deliver one or more electrical pulses or shocks through the patient. This action is also called shocking the patient.

FIG. 1 also shows sample electrotherapy electrodes 104, 108. The electrotherapy electrodes 104, 108 are also called therapy electrodes. When used for defibrillation, the electrotherapy electrodes 104, 108 are also called defibrillation electrodes. The therapy electrodes 104, 108 are coupled to external defibrillator and/or pacer 100 via electrode leads 105. The therapy electrodes 104, 108 can be configured to be worn by the patient 82 in a number of ways. For instance, the defibrillator and/or pacer 100 and the therapy electrodes 104, 108 can be coupled to the support structure 170, directly or indirectly. In other words, the support structure 170 can be configured to be worn by the ambulatory patient 82 so as to maintain at least one of the electrodes 104, 108 on the body of the ambulatory patient 82, while the patient 82 is moving around, etc. The electrode can be thus maintained on the body by being attached to the skin of the patient 82, simply pressed against the skin directly or through garments, etc. In some embodiments the electrode is not necessarily pressed against the skin, but becomes biased that way upon sensing a condition that could merit intervention by the WMS. In addition, many of the components of the defibrillator and/or pacer 100 can be considered coupled to the support structure 170 directly, or indirectly via at least one of the therapy electrodes 104, 108.

When the therapy electrodes 104, 108 make good electrical contact with the body of the patient 82, the defibrillator and/or pacer 100 can administer, via the therapy electrodes 104, 108, one or more brief electric pulses through the body of the patient 82, such as defibrillation pulses and pacing pulses. These pulses are also known as electrotherapy and therapy, and have attributes suitable for their purpose.

A defibrillation pulse 111 is typically strong, having an energy of at least 100 Joule. The defibrillation pulse 111 is also known as shock, defibrillation shock, therapy shock, etc. The defibrillation pulse 111 is intended to go through and restart the heart 85, in an effort to save the life of the patient 82.

A pacing pulse 121 is also shown, but it is not intended to be administered concurrently with the defibrillation pulse 111. The pacing pulse 121 is intended to simply pace the heart 85 if needed, and typically a periodic sequence of pacing pulses is caused to be delivered by appropriately timed discharges. The pacing pulse 121 is shown as smaller than the defibrillation pulse 111 to reflect the fact that pacing pulses have less energy than defibrillation pulses, e.g. namely typically no more than 30 Joule. In reality, the pacing pulse is a discharge from at least two therapy electrodes, which are either the same therapy electrodes 104, 108 as for the defibrillation pulse 111, or different therapy electrodes (not shown in FIG. 1).

A prior art defibrillator typically decides whether to defibrillate or not based on an ECG signal of the patient. However, the external defibrillator and/or pacer 100 may initiate defibrillation, or hold-off defibrillation, or may initiate pacing, based on a variety of inputs, with the ECG signal merely being one of these inputs.

A WMS according to embodiments can obtain data from the patient 82. For collecting such data, the WMS may optionally include at least an outside monitoring device 180. The device 180 is called an "outside" device because it could be provided as a standalone device, for example not within the housing of the defibrillator and/or pacer 100. The device 180 can be configured to sense or monitor at least one local parameter. A local parameter can be a parameter of the patient 82, or a parameter of the WMS, or a parameter of the environment, as will be described later in this document.

For some of these parameters, the device 180 may include one or more sensors or transducers. Each one of such sensors can be configured to sense a parameter of the patient 82, and to render an input responsive to the sensed parameter. In some embodiments the input is quantitative, such as values of a sensed parameter; in other embodiments the input is qualitative, such as informing whether or not a threshold is crossed, and so on. Sometimes these inputs about the patient 82 are also called physiological inputs and patient inputs. In embodiments, a sensor can be construed more broadly, as encompassing more than one individual sensors.

Optionally, the device 180 is physically coupled to the support structure 170. In addition, the device 180 may be communicatively coupled with other components that are coupled to the support structure 170. Such communication can be implemented by a communication module, as will be deemed applicable by a person skilled in the art in view of this description.

In embodiments, one or more of the components of the shown WMS may be customized for the patient 82. This customization may include a number of aspects. For instance, the support structure 170 can be fitted to the body of the patient 82. For another instance, baseline physiological parameters of the patient 82 can be measured for various scenarios, such as when the patient is lying down (various orientations), sitting, standing, walking, running, and so on. These baseline physiological parameters can be the heart rate of the patient 82, motion detector outputs, one for each scenario, etc. The measured values of such baseline physiological parameters can be used to customize the WMS, in order to make its diagnoses more accurate, since patients' bodies differ from one another. Of course, such parameter values can be stored in a memory of the WMS, and so on. Moreover, a programming interface can be made according to embodiments, which receives such measured values of baseline physiological parameters. Such a programming interface may input automatically in the WMS these, along with other data.

Figure 2:
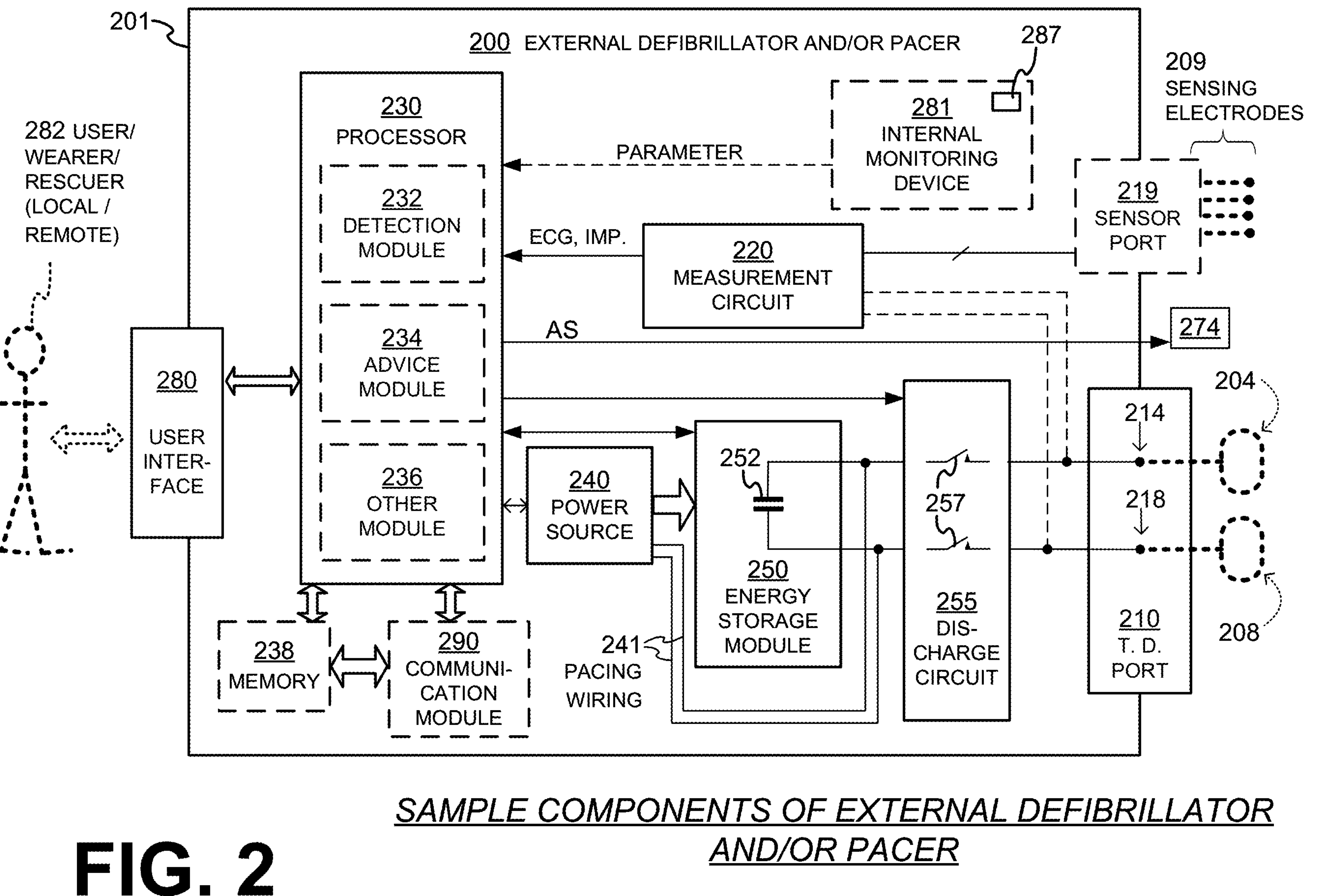
FIG. 2 is a diagram showing sample components of an external defibrillator and/or pacer, such as the one of the WMS of FIG. 1, and which is made according to embodiments.

FIG. 2 is a diagram showing components of an external defibrillator and/or pacer 200, made according to embodiments. These components can be, for example, included in the external defibrillator and/or pacer 100 of FIG. 1. External defibrillator and/or pacer 200 is intended for a patient who would be carrying it on their body, such as ambulatory the patient 82 of FIG. 1. The components shown in FIG. 2 can be provided in a housing 201, which may also be referred to as casing 201.

The defibrillator and/or pacer 200 may include a user interface (UI) 280 for a user 282. User 282 can be the patient 82, also known as patient 282, also known as the wearer 282. Or, the user 282 can be a local rescuer at the scene, such as a bystander who might offer assistance, or a trained person. Or, the user 282 might be a remotely located trained caregiver in communication with the WMS.

The user interface 280 can be made in a number of ways. The user interface 280 may include output devices, which can be visual, audible or tactile, for communicating to a user by outputting images, sounds or vibrations. Images, sounds, vibrations, and anything that can be perceived by user 282 can also be called human-perceptible indications. As such, an output device according to embodiments can be configured to output a human-perceptible indication (HPI). Such HPIs can be used to alert the patient, sound alarms that may be intended also for bystanders, and so on. There are many examples of output devices. For example, an output device can be a light that can be turned on and off, a screen to display what is sensed, detected and/or measured, and provide visual feedback to the local rescuer 282 for their resuscitation attempts, and so on. Another output device can be a speaker, which can be configured to issue voice prompts, alerts, beeps, loud alarm sounds and/or words, and so on. These can also be for bystanders, when defibrillating or just pacing, and so on.

The user interface 280 may further include input devices for receiving inputs from users. Such users can be the patient 82, perhaps a local trained caregiver or a bystander, and so on. Such input devices may include various controls, such as pushbuttons, keyboards, touchscreens, one or more microphones, and so on. An input device can be a cancel switch, which is sometimes called an "I am alive" switch or "live man" switch. In some embodiments, actuating the cancel switch can prevent the impending delivery of a shock, or of pacing pulses. In particular, in some embodiments the speaker is configured to output a warning prompt prior to an impending or planned defibrillation shock or a pacing sequence of pacing pulses being caused to be delivered, and the cancel switch is configured to be actuated by the ambulatory patient 82 in response the warning prompt being output. In such embodiments, the impending or planned defibrillation shock or pacing sequence of the pacing pulses is not caused to be delivered responsive to the cancel switch having been actuated after the warning prompt has been output. Operations of the processor and methods may include causing the speaker to output a warning prompt prior to causing a (planned) pacing sequence of the pacing pulses to be delivered, and determining whether or not the cancel switch has been actuated after the warning prompt has been output.

The defibrillator and/or pacer 200 may include an internal monitoring device 281. The device 281 is called an "internal" device because it is incorporated within the housing 201. The monitoring device 281 can sense or monitor patient parameters such as patient physiological parameters, system parameters and/or environmental parameters, all of which can be called patient data. In other words, the internal monitoring device 281 can be complementary or an alternative to the outside monitoring device 180 of FIG. 1. Allocating which of the parameters are to be monitored by which of the monitoring devices 180, 281 can be done according to design considerations. The device 281 may include one or more sensors, as also described elsewhere in this document.

Patient parameters may include patient physiological parameters. Patient physiological parameters may include, for example and without limitation, those physiological parameters that can be of any help in detecting by the WMS whether or not the patient is in need of a shock or other intervention or assistance. Patient physiological parameters may also optionally include the patient's medical history, event history and so on. Examples of such parameters include the patient's ECG, blood oxygen level, blood flow, blood pressure, blood perfusion, pulsatile change in light transmission or reflection properties of perfused tissue, heart sounds, heart wall motion, breathing sounds and pulse. Accordingly, the monitoring devices 180, 281 may include one or more sensors configured to acquire patient physiological signals. Examples of such sensors or transducers include one or more electrodes to detect ECG data, a perfusion sensor, a pulse oximeter, a device for detecting blood flow (e.g. a Doppler device), a sensor for detecting blood pressure (e.g. a cuff), an optical sensor, illumination detectors and sensors perhaps working together with light sources for detecting color change in tissue, a motion sensor, a device that can detect heart wall movement, a sound sensor, a device with a microphone, an $SpO_2$ sensor, and so on. In view of this disclosure, it will be appreciated that such sensors can help detect the patient's pulse, and can therefore also be called pulse detection sensors, pulse sensors, and pulse rate sensors. In addition, a person skilled in the art may implement other ways of performing pulse detection.

In some embodiments, the local parameter is a trend that can be detected in a monitored physiological parameter of the patient 282. A trend can be detected by comparing values of parameters at different times over short and long terms. Parameters whose detected trends can particularly help a cardiac rehabilitation program include: a) cardiac function (e.g. ejection fraction, stroke volume, cardiac output, etc.); b) heart rate variability at rest or during exercise; c) heart rate profile during exercise and measurement of activity vigor, such as from the profile of an accelerometer signal and informed from adaptive rate pacemaker technology; d) heart rate trending; e) perfusion, such as from $SpO_2$, $CO_2$, or other parameters such as those mentioned above, f) respiratory function, respiratory rate, etc.; g) motion, level of activity; and so on. Once a trend is detected, it can be stored and/or reported via a communication link, along perhaps with a warning if warranted. From the report, a physician monitoring the progress of the patient 282 will know about a condition that is either not improving or deteriorating.

Patient state parameters include recorded aspects of the patient 282, such as motion, posture, whether they have spoken recently plus maybe also what they said, and so on, plus optionally the history of these parameters. Or, one of these monitoring devices could include a location sensor such as a Global Positioning System (GPS) location sensor. Such a sensor can detect the location, plus a speed can be detected as a rate of change of location over time. Many motion detectors output a motion signal that is indicative of the motion of the detector, and thus of the patient's body. Patient state parameters can be very helpful in narrowing down the determination of whether SCA is indeed taking place.

A WMS made according to embodiments may thus include a motion detector. In embodiments, a motion detector can be implemented within the outside monitoring device 180 or within the internal monitoring device 281. A motion detector of a WMS according to embodiments can be configured to detect a motion event. A motion event can be defined as is convenient, for example a change in motion from a baseline motion or rest, etc. In such cases, a sensed patient parameter is motion. Such a motion detector can be made in many ways as is known in the art, for example by using an accelerometer and so on. In this example, a motion detector 287 is implemented within the monitoring device 281.

System parameters of a WMS can include system identification, battery status, system date and time, reports of self-testing, records of data entered, records of episodes and intervention, and so on. In response to the detected motion event, the motion detector may render or generate, from the detected motion event or motion, a motion detection input that can be received by a subsequent device or functionality.

Environmental parameters can include ambient temperature and pressure. Moreover, a humidity sensor may provide information as to whether or not it is likely raining. Presumed patient location could also be considered an environmental parameter. The patient location could be presumed, if the monitoring device 180 or 281 includes a GPS location sensor as per the above, and if it is presumed or sensed that the patient is wearing the WMS.

The defibrillator and/or pacer 200 typically includes a therapy delivery port 210. The therapy delivery port 210 can be a socket in the housing 201, or other equivalent structure. The therapy delivery port 210 includes electrical nodes 214, 218. Leads of the therapy electrodes 204, 208, such as the leads 105 of FIG. 1, can be plugged into the therapy delivery port 210, so as to make electrical contact with the nodes 214, 218, respectively. It is also possible that the therapy electrodes 204, 208 are connected continuously to the therapy delivery port 210, instead. Either way, the therapy delivery port 210 can be used for guiding, via electrodes, to the wearer at least some of the electrical charge that has been stored in an energy storage module 250 that is described more fully later in this document. The electric charge will be the shock for defibrillation, pacing, and so on.

The defibrillator and/or pacer 200 may optionally also have a sensor port 219 in the housing 201, which is also sometimes known as an ECG port. The sensor port 219 can be adapted for plugging in the sensing electrodes 209, which are also known as ECG electrodes and ECG leads. The ECG electrodes 209 in this example are distinct from the therapy electrodes 104, 108. It is also possible that the sensing electrodes 209 can be connected continuously to the sensor port 219, instead. The sensing electrodes 209 can be types of transducers that can help sense an ECG signal of the patient, e.g. a 12-lead signal, or a signal from a different number of leads, especially if they make good electrical contact with the body of the patient and in particular with the skin of the patient. As with the therapy electrodes 204, 208, the support structure can be configured to be worn by the patient 282 so as to maintain the sensing electrodes 209 on a body of the patient 282. For example, the sensing electrodes 209 can be attached to the inside of the support structure 170 for making good electrical contact with the patient, similarly with the therapy electrodes 204, 208.

Optionally a WMS according to embodiments also includes a fluid that it can deploy automatically between the electrodes and the patient's skin. The fluid can be conductive, such as by including an electrolyte, for establishing a better electrical contact between the electrodes and the skin. Electrically speaking, when the fluid is deployed, the electrical impedance between each electrode and the skin is reduced. Mechanically speaking, the fluid may be in the form of a low-viscosity gel. As such, it will not flow too far away from the location it is released, after being deployed. The fluid can be used for both the therapy electrodes 204, 208, and for the sensing electrodes 209.

The fluid may be initially stored in a fluid reservoir, not shown in FIG. 2. Such a fluid reservoir can be coupled to the support structure. In addition, a WMS according to embodiments further includes a fluid deploying mechanism 274. The fluid deploying mechanism 274 can be configured to cause at least some of the fluid to be released from the reservoir, and be deployed near one or both of the patient locations to which the therapy electrodes 204, 208 are configured to be attached to the patient. In some embodiments, the fluid deploying mechanism 274 is activated prior to the electrical discharge responsive to receiving an activation signal AS from a processor 230, which is described more fully later in this document.

In some embodiments, defibrillator and/or pacer 200 also includes a measurement circuit 220, as one or more of its modules working together with its sensors or transducers. The measurement circuit 220 senses one or more electrical physiological signals of the patient from the sensor port 219, if provided. Even if the defibrillator and/or pacer 200 lacks a sensor port, the measurement circuit 220 may optionally obtain physiological signals through the nodes 214, 218 instead, when the therapy electrodes 204, 208 are attached to the patient. In these cases, the input reflects an ECG measurement. The patient parameter can be an ECG, which can be sensed as a voltage difference between electrodes 204, 208. In addition, the patient parameter can be an impedance (IMP. or Z), which can be sensed between the electrodes 204, 208 and/or between the connections of the sensor port 219 considered pairwise. Sensing the impedance can be useful for detecting, among other things, whether these electrodes 204, 208 and/or the sensing electrodes 209 are not making good electrical contact with the patient's body at the time. These patient physiological signals may be sensed when available. The measurement circuit 220 can then render or generate information about them as inputs, data, other signals, etc. As such, the measurement circuit 220 can be configured to render a patient input responsive to a patient parameter sensed by a sensor. In some embodiments, the measurement circuit 220 can be configured to render a patient input, such as values of an ECG signal, responsive to the ECG signal sensed by the sensing electrodes 209. More strictly speaking, the information rendered by the measurement circuit 220 is output from it, but this information can be called an input because it is received as an input by a subsequent stage, device or functionality.

The defibrillator and/or pacer 200 also includes a processor 230. The processor 230 may be implemented in a number of ways. Such ways include, by way of example and not of limitation, digital and/or analog processors such as microprocessors and Digital Signal Processors (DSPs), controllers such as microcontrollers, software running in a machine, programmable circuits such as Field Programmable Gate Arrays (FPGAs), Field-Programmable Analog Arrays (FPAAs), Programmable Logic Devices (PLDs), Application Specific Integrated Circuits (ASICs). In various embodiments, the processor may be implemented using any combination of one or more of the above types of processors, and so on. In some embodiments, the processor may be implemented using multiple electronic devices distributed in various parts of external defibrillator and/or pacer 200.

The processor 230 may include, or have access to, a non-transitory storage medium, such as a memory 238 that is described more fully later in this document. Such a memory can have a non-volatile component for storage of machine-readable and machine-executable instructions. A set of such instructions can also be called a program. The instructions, which may also be referred to as "software," generally provide functionality by performing acts, operations and/or methods as may be disclosed herein or understood by one skilled in the art in view of the disclosed embodiments. In some embodiments, and as a matter of convention used herein, instances of the software may be referred to as a "module" and by other similar terms. Generally, a module includes a set of the instructions so as to offer or fulfill a particular functionality. Embodiments of modules and the functionality delivered are not limited by the embodiments described in this document.

The processor 230 can be considered to have a number of modules. One such module can be a detection module 232. The detection module 232 can include a Ventricular Fibrillation (VF) detector. The patient's sensed ECG from measurement circuit 220, which can be available as inputs, data that reflect values, or values of other signals, may be used by the VF detector to determine whether the patient is experiencing VF. Detecting VF is useful, because VF typically results in SCA. The detection module 232 can also include a Ventricular Tachycardia (VT) detector for detecting VT, and so on.

Another such module in processor 230 can be an advice module 234, which generates advice for what to do. The advice can be based on outputs of the detection module 232. There can be many types of advice according to embodiments. In some embodiments, the advice is a shock/no shock determination that processor 230 can make, for example via advice module 234. The shock/no shock determination can be made by executing a stored Shock Advisory Algorithm. A Shock Advisory Algorithm can make a shock/no shock determination from one or more ECG signals that are captured according to embodiments, and determine whether or not a shock criterion is met. The determination can be made from a rhythm analysis of the captured ECG signal or otherwise. For example, there can be shock decisions for VF, VT, etc.

In some embodiments, when the determination is to shock, an electrical charge is delivered to the patient. Delivering the electrical charge is also known as discharging and shocking the patient. As mentioned above, such can be for defibrillation, pacing, and so on.

In perfect conditions, a very reliable shock/no shock determination can be made from a segment of the sensed ECG signal of the patient. In practice, however, the ECG signal is often corrupted by electrical noise, which makes it difficult to analyze. Too much noise sometimes causes an incorrect detection of a heart arrhythmia, resulting in a false alarm to the patient. Noisy ECG signals may be handled as described in published US patent application No. US 2019/0030351 A1, and No. US 2019/0030352 A1, and which are incorporated herein by reference.

The processor 230 can include additional modules, such as other module 236, for other functions. In addition, if the internal monitoring device 281 is indeed provided, the processor 230 may receive its inputs, etc.

The defibrillator and/or pacer 200 optionally further includes a memory 238, which can work together with the processor 230. The memory 238 may be implemented in a number of ways. Such ways include, by way of example and not of limitation, volatile memories, Nonvolatile Memories (NVM), Read-Only Memories (ROM), Random Access Memories (RAM), magnetic disk storage media, optical storage media, smart cards, flash memory devices, any combination of these, and so on. The memory 238 is thus a non-transitory storage medium. The memory 238, if provided, can include programs for the processor 230, which the processor 230 may be able to read and execute. More particularly, the programs can include sets of instructions in the form of code, which the processor 230 may be able to execute upon reading. Executing is performed by physical manipulations of physical quantities, and may result in functions, operations, processes, acts, actions and/or methods to be performed, and/or the processor to cause other devices or components or blocks to perform such functions, operations, processes, acts, actions and/or methods. The programs can be operational for the inherent needs of the processor 230, and can also include protocols and ways that decisions can be made by the advice module 234. In addition, the memory 238 can store prompts for the user 282, if this user is a local rescuer. Moreover, the memory 238 can store data. This data can include patient data, system data and environmental data, for example as learned by the internal monitoring device 281 and the outside monitoring device 180. The data can be stored in the memory 238 before it is transmitted out of defibrillator and/or pacer 200, or be stored there after it is received by the defibrillator and/or pacer 200.

The defibrillator and/or pacer 200 can optionally include a communication module 290, for establishing one or more wired or wireless communication links with other devices of other entities, such as a remote assistance center, Emergency Medical Services (EMS), and so on. The communication links can be used to transfer data and commands. The data may be patient data, event information, therapy attempted, CPR performance, system data, environmental data, and so on. For example, the communication module 290 may transmit wirelessly, e.g. on a daily basis, heart rate, respiratory rate, and other vital signs data to a server accessible over the internet, for instance as described in US 20140043149. This data can be analyzed directly by the patient's physician and can also be analyzed automatically by algorithms designed to detect a developing illness and then notify medical personnel via text, email, phone, etc. The module 290 may also include such interconnected sub-components as may be deemed necessary by a person skilled in the art, for example an antenna, portions of a processor, supporting electronics, outlet for a telephone or a network cable, etc.

The defibrillator and/or pacer 200 may also include a power source 240, which is configured to provide electrical charge in the form of a current. To enable portability of the defibrillator and/or pacer 200, the power source 240 typically includes a battery. Such a battery is typically implemented as a battery pack, which can be rechargeable or not. Sometimes a combination is used of rechargeable and non-rechargeable battery packs. Other embodiments of the power source 240 can include an AC power override, for where AC power will be available, an energy-storing capacitor, and so on. Appropriate components may be included to provide for charging or replacing the power source 240. In some embodiments, the power source 240 is controlled and/or monitored by the processor 230.

The defibrillator and/or pacer 200 may additionally include an energy storage module 250. The energy storage module 250 can be coupled to the support structure of the WMS, for example either directly or via the electrodes and their leads. The energy storage module 250 can be coupled to receive the electrical charge provided by the power source 240. The energy storage module 250 can be configured to store the electrical charge received by the power source. As such, the energy storage module 250 is where some electrical energy can be stored temporarily in the form of an electrical charge, when preparing it for discharge to administer a shock. In embodiments, the module 250 can be charged from the power source 240 to the desired amount of energy, for instance as controlled by the processor 230. In typical implementations, the module 250 includes a capacitor 252, which can be a single capacitor or a system of capacitors, and so on. In some embodiments, the energy storage module 250 includes a device that exhibits high power density, such as an ultracapacitor. As described above, the capacitor 252 can store the energy in the form of an electrical charge, for delivering to the patient.

A decision to shock can be made responsive to the shock criterion being met, as per the above-mentioned determination. When the decision is to shock, the processor 230 can be configured to cause at least some or all of the electrical charge stored in the module 250 to be discharged through the patient 82 while the support structure is worn by the patient 82, so as to deliver the shock 111 to the patient 82.

For causing the discharge, the defibrillator and/or pacer 200 moreover includes a discharge circuit 255. When the decision is to shock, the processor 230 can be configured to control the discharge circuit 255 to discharge through the patient at least some of all of the electrical charge stored in the energy storage module 250, especially in a desired waveform. When the decision is to merely pace, i.e., to deliver pacing pulses, the processor 230 can be configured to cause control the discharge circuit 255 to discharge through the patient at least some of the electrical charge provided by the power source 240. Since pacing requires lesser charge and/or energy than a defibrillation shock, in some embodiments pacing wiring 241 is provided from the power source 240 to the discharge circuit 255. The pacing wiring 241 is shown as two wires that bypass the energy storage module 250. As such, the energy for the pacing is provided by the power source 240 either directly via the pacing wiring 241, or through the discharge circuit 250. And, in some embodiments where only a pacer is provided, the energy storage module 250 is not needed, and enough pacing current may be provided from the power source 240. Either way, discharging can be to the nodes 214, 218, and from there to the therapy electrodes 204, 208, so as to cause a shock to be delivered to the patient. The circuit 255 can include one or more switches 257. The switches 257 can be made in a number of ways, such as by an H-bridge, and so on. In some embodiments, different ones of the switches 257 may be used for a discharge where a defibrillation shock is caused to be delivered, than for a discharge where the much weaker pacing pulses are caused to be delivered. The circuit 255 could also be thus controlled via the processor 230, and/or the user interface 280.

The pacing capability can be implemented in a number of ways. ECG sensing may be done in the processor, as mentioned elsewhere in this document, or separately, for demand or synchronous pacing. In some embodiments, however, pacing can be asynchronous. Pacing can be software controlled, e.g., by managing the defibrillation path, or a separate pacing therapy circuit (not shown) could be included, which can receive the ECG sensing.

A time waveform of the discharge may be controlled by thus controlling discharge circuit 255. The amount of energy of the discharge can be controlled by how much energy storage module has been charged, and also by how long the discharge circuit 255 is controlled to remain open.

The defibrillator and/or pacer 200 can optionally include other components.

Figure 3:
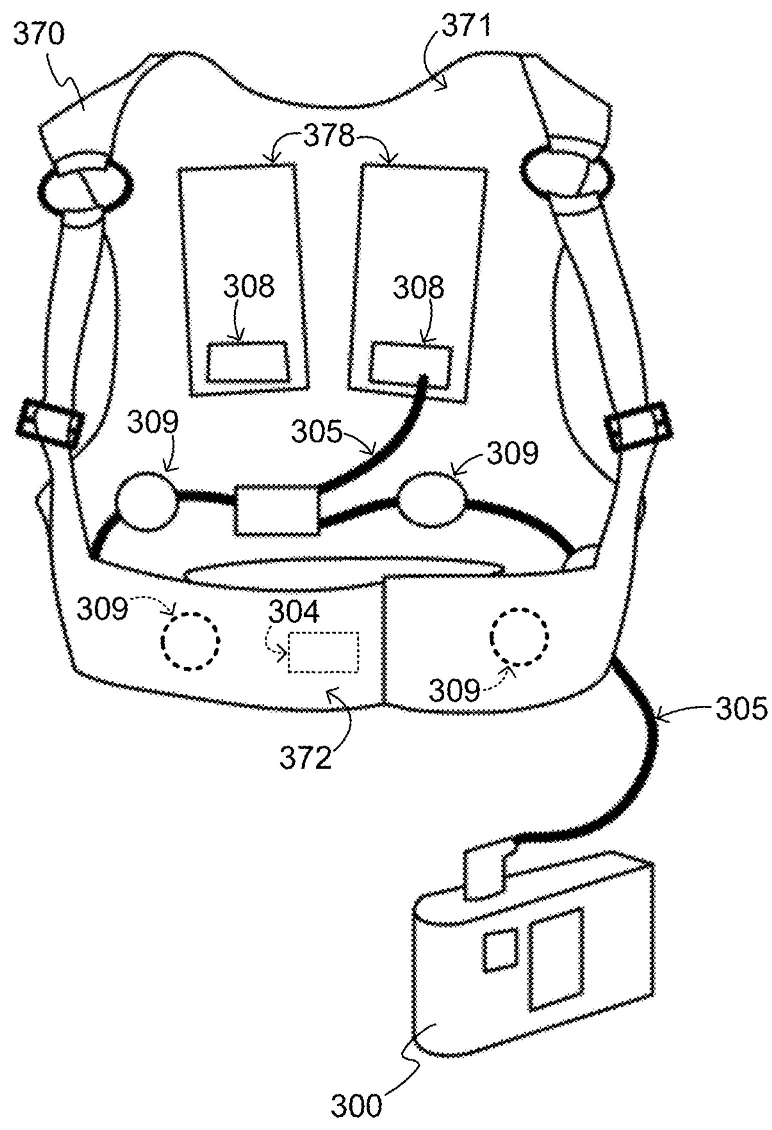
FIG. 3 is a diagram of sample embodiments of components of a WMS.

FIG. 3 is a diagram of sample embodiments of components of an WMS. A support structure 370 includes a vest-like wearable garment. The support structure 370 has a back side 371, and a front side 372 that closes in front of the chest of the patient.

The WMS of FIG. 3 also includes an external defibrillator and/or pacer 300. FIG. 3 does not show any support for external defibrillator and/or pacer 300, which may be carried in a purse, on a belt, by a strap over the shoulder, on the support structure 370, and so on. Wires 305 connect the external defibrillator and/or pacer 300 to electrodes 304, 308, 309. Of those, the electrodes 304, 308 are therapy electrodes, and the electrodes 309 are ECG sensing electrodes. The therapy electrodes 104, 108, 204, 208, 304, 308 can also be called discharge electrodes.

The support structure 370 is configured to be worn by the ambulatory patient so as to maintain the electrodes 304, 308, 309 on a body of the patient. Indeed, the back therapy electrodes 308 are maintained in pockets 378. Of course, the inside of the pockets 378 can be made with loose netting, so that the electrodes 308 can contact the back of the patient, especially with the help of the conductive fluid that has been deployed. In addition, the sensing electrodes 309 are maintained in positions that surround the patient's torso, for sensing ECG signals and/or the impedance of the patient.

ECG signals in a WMS may include too much electrical noise to be useful. To ameliorate the problem, multiple ECG sensing electrodes 309 are provided, for presenting many options to the processor 230. These options are different vectors for sensing the ECG signal, as described now in more detail.

WMSs according to embodiments advantageously also include one or more pacing capabilities. For pacing, instead of defibrillating the patient with a strong defibrillation pulse, at least some of the stored electrical charge is caused to be discharged via at least two of the therapy electrodes 104, 108, 204, 208, 304, 308 through the ambulatory patient 82, so as to deliver to the ambulatory patient 82 a pacing sequence of pacing pulses. In other words, the pacing pulses may be delivered via the therapy electrodes. The pacing pulses may have certain energies, respectively. The energies may be less than 30 Joule, and usually about 10 J. The pacing pulses may have certain spacings between successive ones of them. These spacings define the pacing period, and thus the pacing rate of the pacing sequence. The pacing pulses may be periodic, but there is no requirement for them to be so.

In embodiments, the WMS may detect when the patient's heart rhythm starts to deteriorate, but before the rhythm reaches the state where the patient needs to be defibrillated. In such embodiments, the WMS may pace the patient first, and hopefully not have to resort to the full intervention of defibrillation. Of course, if the patient does not respond to the pacing, the WMS may then later cause a defibrillation shock to be delivered.

In some embodiments, the pacing is controlled by the processor 230. It is the processor 230 that can analyze the ECG signal, or portions of it, that are sensed by the ECG electrodes. The analysis can be to determine whether or not the ECG signal meets one or more criteria, which is also known as analyzing the ECG signal against these criteria. The analysis by the processor 230 can also be for operations shown in the flowcharts of this document, including compute a heart rate, turn on and off QRS detection, and so on. Responsive to the analysis, the processor 230 can be configured to cause pacing pulses to be delivered, with the desired energy, spacings between successive ones of and waveform. The processor 230 can be further configured to change the pacing pulses, stop them, defibrillate, and so on, in addition to all other functions such as cause communication and so on.

In some embodiments, a WMS detects a bradycardia of one or more types, and then confirms the detection, before pacing to treat the detected bradycardia. The detected bradycardia here can be heart arrhythmias where the heart is beating spontaneously more slowly than normal, or not at all, and include at least bradycardia, extreme bradycardia and asystole. Examples are now described.

Figure 4:
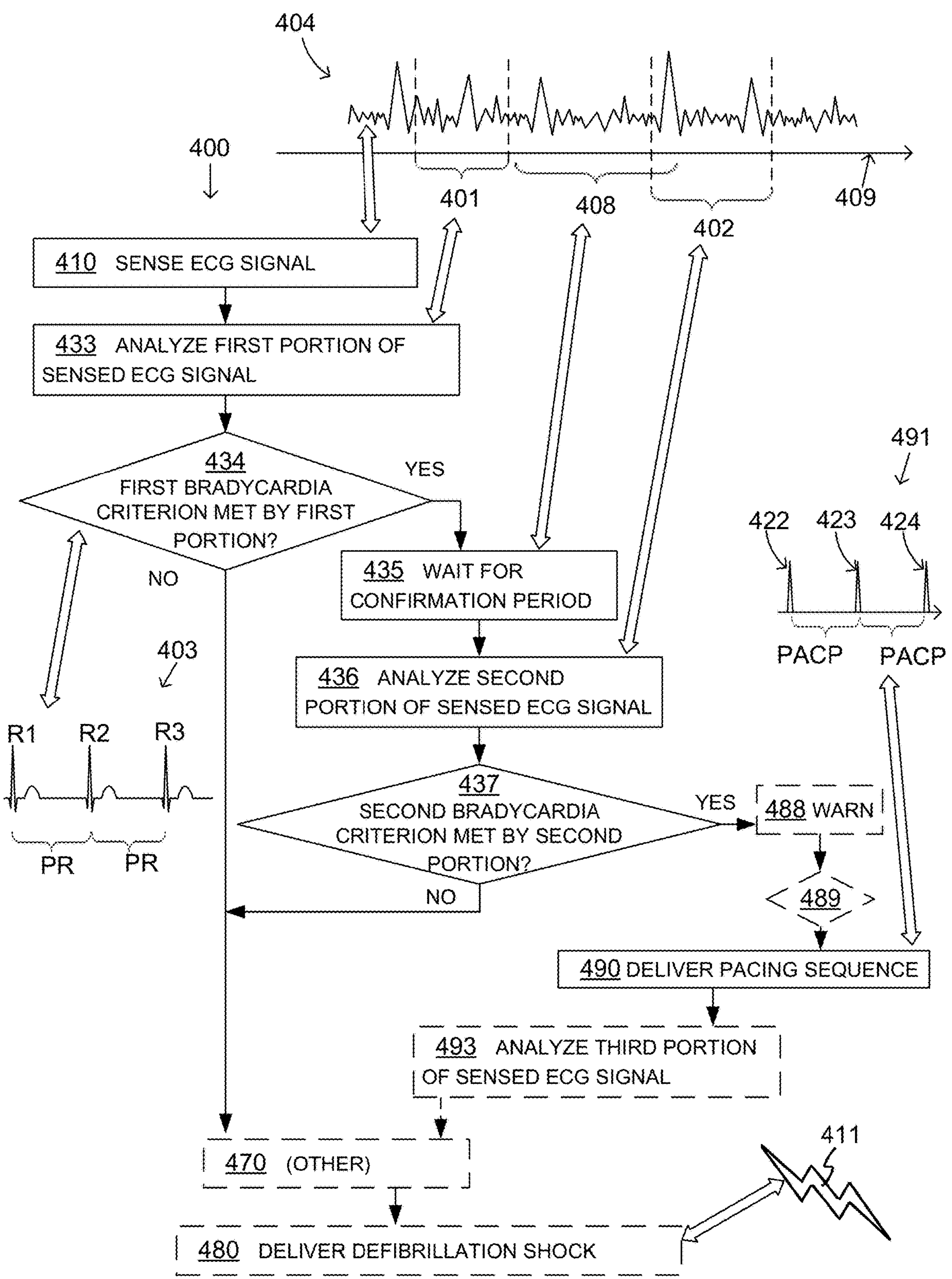
FIG. 4 shows a flowchart for illustrating sample methods according to embodiments, and it further augments the flowchart with small diagrams and/or icons of elements that can be related to individual operations of the flowchart.

FIG. 4 shows a flowchart 400 for describing methods according to embodiments. In addition, FIG. 4 shows a time diagram of a sample ECG signal 404 along a time axis 409. Also, FIG. 4 shows a small fraction of a sample pacing sequence 491, in the form of a timing diagram. Moreover, FIG. 4 shows an icon of a defibrillation shock 411, similar to the defibrillation shock 111 of FIG. 1.

The method of flowchart 400 can start at an operation 410, where an ECG signal 404 of an ambulatory patient can be sensed.

According to another operation 433, a first portion 401 of the sensed ECG signal 404 can be analyzed against a first bradycardia criterion. The first bradycardia criterion may be implemented in a number of ways. In some embodiments, the first bradycardia criterion includes having detected, in the first portion 401 of the ECG signal 404, heartbeats that have a heart rate of less than 40 beats per minute (bpm). Or, less than 30 bpm. Or, less than 20 bpm for extreme bradycardia, and so on. Notably, when the bradycardia criterion includes having detected a heart rate of less than 20 bpm, that could independently be also a criterion for asystole. In embodiments, therefore, asystole may be detected as well.

For better explanation of bradycardia criteria, the waveform 403 is an idealized version of what ECG signal 404 might be, if the patient were perfectly healthy, at a normal time, and with no noise present. The analysis attempts to detect, and here would find, three R peaks R1, R2, R3. Between two successive ones of them, these three R peaks R1, R2, R3 have spacings PR. These spacings need not be identical, of course, but they usually are substantially equal. The average of these spacings would correspond to the heart rate, which then would be applied to the criterion.

According to another operation 434, which is shown as a decision diamond 434, it can be determined whether or not the first bradycardia criterion is met at the operation 433. If not then, at another operation 480, a defibrillation shock 411 may be later delivered, in embodiments where a defibrillator is also provided. It can be delivered later, because some time may pass with other events, and optional other operations 470 may be performed in the interim, such as other diagnoses, prompts, and treatments. For instance, at the operation 470, a defibrillation criterion may be first determined to be met. The defibrillation criterion may be met later, and not in connection to any bradycardia. For performing the operation 480, the processor can be configured to cause at least some of the stored electrical charge to be discharged via at least two of the therapy electrodes through the ambulatory patient, so as to deliver to the ambulatory patient a defibrillation shock 411 having an energy of at least 100 Joule.

If, at the operation 434, it is determined that the first bradycardia criterion of the operation 433 is met then, according to another operation 435, there can be waiting, for a confirmation period 408 of at least 10 sec. The confirmation period 408 can last longer, for example at least 20 sec, at least 50 sec such as 60 sec, and so on. Again, the waiting for the confirmation period can be performed responsive to the first portion 401 of the analyzed ECG signal 404 meeting the first bradycardia criterion of the operation 433.

According to another operation 436, a second portion 402 of the sensed ECG signal 404 may be analyzed. At least a fraction of the second portion 402 of the sensed ECG signal 404 may have been sensed during the confirmation period 408. Or, even the entire second portion 402 of the sensed ECG signal 404 may been sensed during the confirmation period 408.

At the operation 436 the second portion 402 may be analyzed against a second bradycardia criterion. The second bradycardia criterion can be the same, or different, as the first bradycardia criterion, of course as applied to the second portion 402 of the ECG signal instead of to the first portion 401.

According to another operation 437, it can be determined whether or not the second bradycardia criterion is met at the operation 436. If not then, then execution may proceed to the operation 480, similarly with a no answer from the operation 434.

If, at the operation 437, it is determined that the second bradycardia criterion of the operation 436 is met, then another operation 490 may be performed. Prior to the operation 490, according to an optional operation 488, the ambulatory patient 82 may be warned of the impending pacing. In particular, a speaker of the UI 280 may output a warning prompt prior to the pacing sequence of the pacing pulses of the operation 490 being caused to be delivered. According to an optional operation 489, the processor can be further configured to determine whether or not the cancel switch has been actuated after the warning prompt has been output. In such embodiments, the pacing sequence of the pacing pulses is not caused to be delivered responsive to determining that the cancel switch has been actuated after the warning prompt has been output. The operation 488 may be performed at different times prior to the operation 488; in particular, the warning prompt can be output prior to, concurrently with, or after analyzing the second portion of the sensed ECG signal against the second bradycardia criterion, and so on. In this diagram, the operation 488 is shown as being performed after the operation 437, but that is only a non-limiting example.

Then, according to another operation 490, at least some of the electrical charge provided by the source can be caused to be discharged via at least two of the therapy electrodes through the ambulatory patient so as to deliver to the ambulatory patient a pacing sequence 491 of pacing pulses 422, 423, 424. The pacing pulses 422, 423, 424 may have certain energies, at least some of the certain energies being at most 30 Joule, as per the above for pacing pulses. The energy storage module 252 may be recharged after one or more pacing pulses. Again, the pacing sequence 491 can be caused to be delivered responsive to the second portion 402 of the analyzed ECG signal 404 meeting the second bradycardia criterion of the operation 437. In embodiments, low-rate (e.g., 40 bpm), life-sustaining, pacing therapy can be thus provided in response to sustained, extremely low intrinsic heart rates (e.g., <30 bpm) or extended periods of asystole.

The pacing pulses 422, 423, 424 may have certain spacings PACP between them, which are also known as pacing periods. These may be equal to each other, or not. In some embodiments, the certain spacings PACP between the pacing pulses 422, 423, 424 of the pacing sequence 491 amount to a pacing rate having a value between 30 beats per minute (bpm) and 90 bpm. Similarly a group of, say, 10 such pacing pulses taken together may have 9 spacings among them, the 9 spacings having an average spacing that amounts to such a pacing rate.

According to another, optional operation 493, the pacing sequence 491 has a certain duration, which means it ends at some point. In such embodiments, the processor can be further configured to analyze, after the certain duration, a third portion of the sensed ECG signal, which is sensed after the second portion 402 of the sensed ECG signal 404.

Responsive to a result of the analysis of the operation 493, a number of operations may be performed. In some instances, the defibrillation shock of operation 480 is caused to be delivered, for instance to terminate any starting ventricular tachycardia (VT) or ventricular fibrillation (VF). In other instances, pacing stops, and other examples will be described below with reference to FIG. 8. In other instances, such as if bradycardia is detected, pacing resumes, to deliver to the patient another pacing sequence of pacing pulses of the same or different parameters. Plus, this sequence of "pace, stop, sense ECG, analyze ECG, then pace again if needed" may also be performed without the waiting for the confirmation period.

In other embodiments, at the operation 493, the third portion is analyzed against an escape pacing criterion. The escape pacing criterion may include having detected, in the third portion of the ECG signal, heartbeats that have a heart rate of at least 30 beats per minute (bpm). Or, at least 40 bpm. In such embodiments, responsive to the third portion of the analyzed ECG signal meeting the escape pacing criterion, the processor might not cause any of the electrical charge provided by the source to be discharged through the ambulatory patient for at least 60 sec, or even longer.

It will be appreciated that, when the sample ECG signal 404 is sensed in some of the embodiments of FIG. 4, no pacing is taking place. As such, the sample ECG signal 404 does not include any artifacts, such as little spikes that have been added from the pacing.

This is not always the case with embodiments. In some embodiments, the ECG signal is sensed while pacing is applied. Sample ECG signals are now shown and described, where pacing markers have been added to shown when pacing took place.

Figure 5:
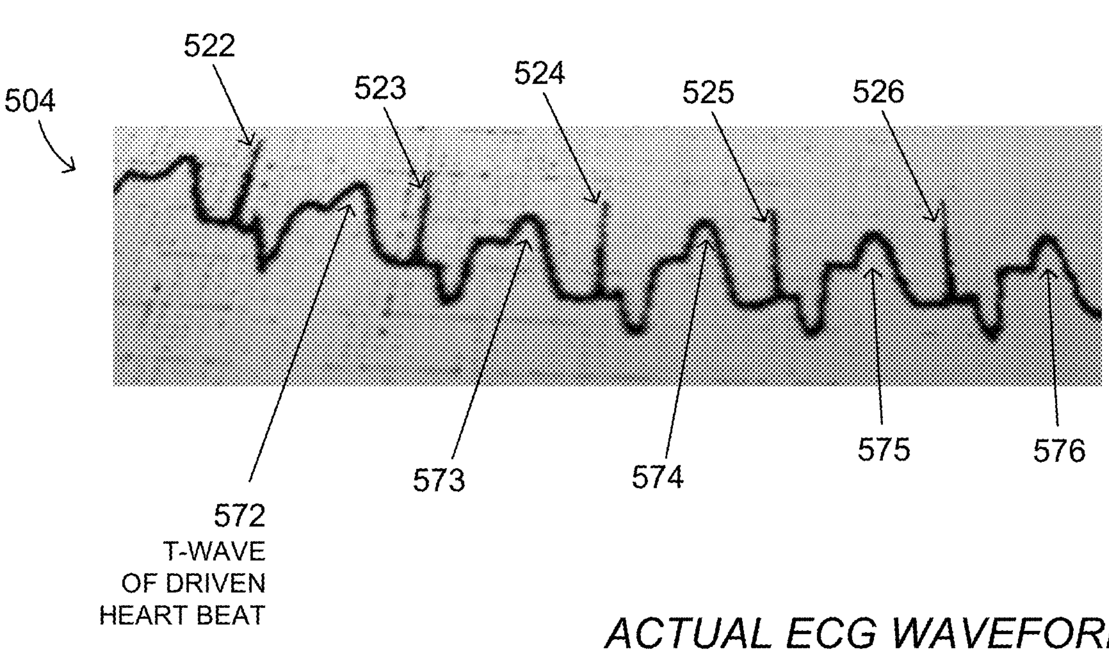
FIG. 5 is a diagram of a waveform of a sample actual ECG signal, sensed while the patient is being paced according to embodiments, and with no appreciable electrical noise present.

FIG. 5 is a diagram of a waveform of a sample actual ECG signal 504, which is sensed while the patient is being paced according to embodiments. In this example there is no appreciable noise.

In FIG. 5, pacing markers 522, 523, 524, 525, 526 can be discerned easily thanks to the lack of noise. It will be appreciated that, in this example, the pacing has likely captured the heart, which means that the pacing markers 522, 523, 524, 525, 526 actually drive corresponding heartbeats, whose T waves are denoted as 572, 573, 574, 575, 576. The R waves that take place before these T waves are obscured by the pacer refractory period, and are thus not visible in FIG. 5. Such capture does not happen always.

One more observation about the pacing rate in FIG. 5 is that the pacing is relatively fast. Each time, the next pacing pulse is delivered very soon after the previous driven heartbeat. This does not allow any opportunity for intrinsic heartbeats, for reasons that are explained later in this document.

Figure 6:
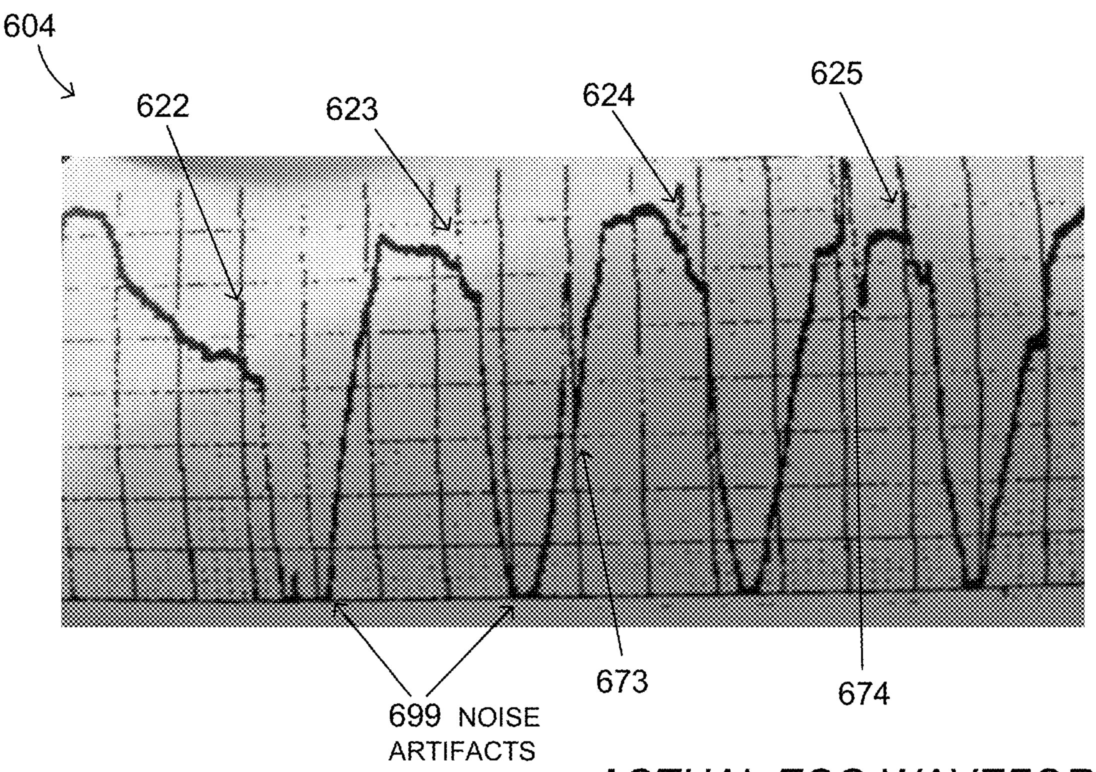
FIG. 6 is a diagram of a waveform of a sample actual ECG signal, sensed while the patient is being paced according to embodiments, and with electrical noise present.

FIG. 6 is a diagram of a waveform of a sample actual ECG signal 604, which is sensed while the patient is being paced according to embodiments. In this example there is appreciable noise, as would be the case with the ambulatory patient being conscious and moving.

In FIG. 6, pacing markers 622, 623, 624, 625 are pointed out. There are large noise artifacts 699. Here two intrinsic heartbeats 673, 674 are detected, and this is an example of pacing with no capture.

From FIG. 6, the deleterious effects of electrical noise can be appreciated. Indeed, electrical noise in the ECG signal may cause detection to not detect heartbeats, or detect heartbeats where there are none, and accordingly misdiagnose the condition of the patient, with a potentially deadly outcome.

In some embodiments, a WMS applies the same pacing sequence to treat bradycardia and asystole. Optionally, it also applies this pacing sequence after a defibrillation shock. Examples are now described.

Figure 7:
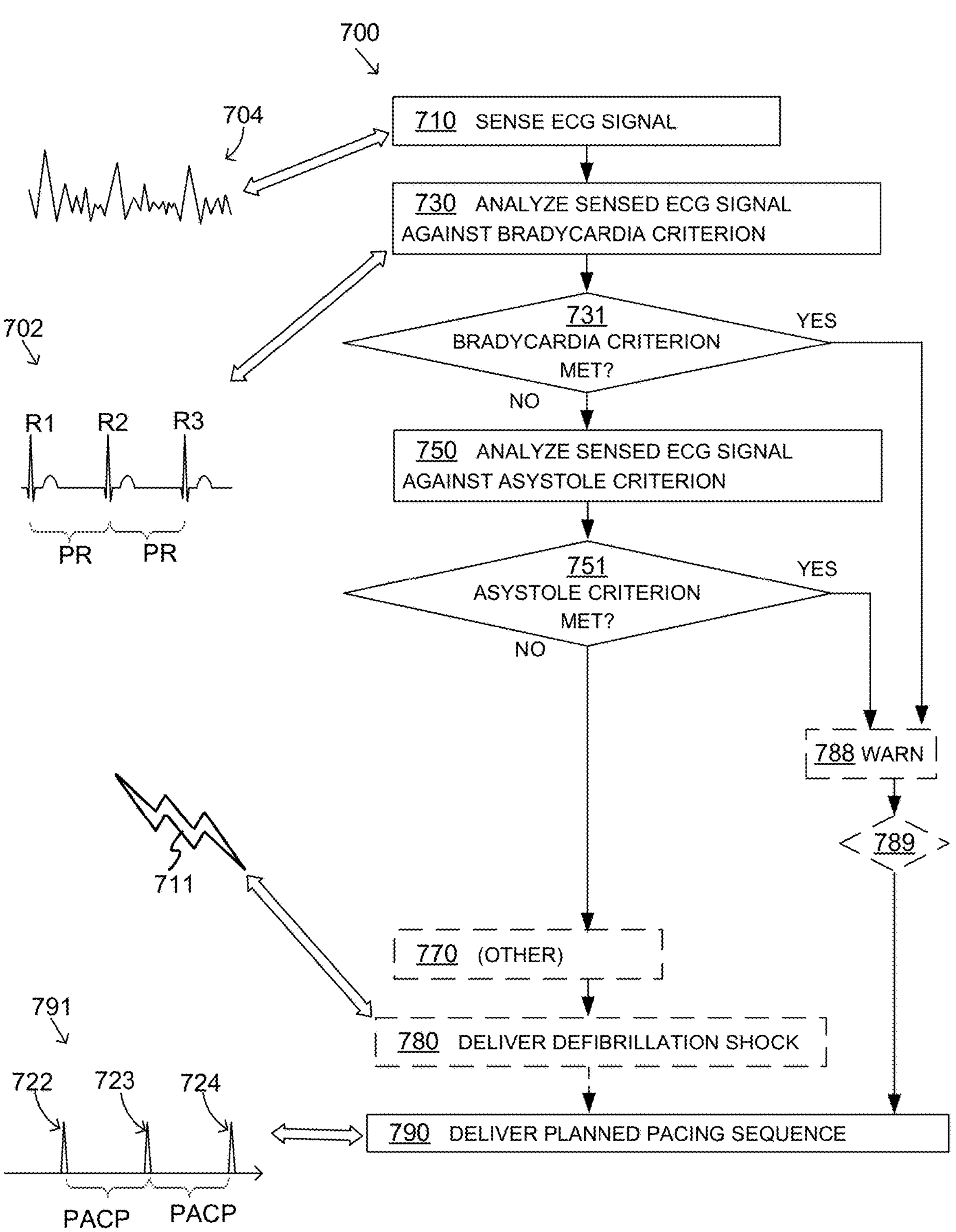
FIG. 7 shows a flowchart for illustrating sample methods according to embodiments, and it further augments the flowchart with small diagrams and/or icons of elements that can be related to individual operations of the flowchart.

FIG. 7 shows a flowchart 700 for describing methods according to embodiments. In addition, FIG. 7 shows a sample ECG signal 704, and a small idealized ECG waveform 702 for explaining a bradycardia criterion. Also, FIG. 7 shows a small fraction of a sample pacing sequence 791 in the form of a timing diagram. Moreover, FIG. 7 shows an icon of a defibrillation shock 711, similar to those of the defibrillation shocks 111, 411.

The method of flowchart 700 can start at an operation 710, where an ECG signal 704 of an ambulatory patient can be sensed. The ECG signal 704 can be as described earlier, for instance for ECG signal 404.

According to another operation 730, the sensed ECG signal 704 can be analyzed against a bradycardia criterion, to detect whether the patient is suffering from bradycardia. The bradycardia criterion may be implemented in a number of ways. For instance, the bradycardia criterion may be that a detected heart rate is less than 50 bpm, but also larger than 15 bpm. Less than 15 bpm might be bradycardia or asystole. The heartbeats may be detected from their most prominent feature, namely the R peaks of QRS complexes. Again, the waveform 702 is an idealized version of what ECG signal 704 might be; in this example, the waveform 702 is also identical to the waveform 403, and so on.

According to another operation 731, it can be determined whether or not the bradycardia criterion is met at the operation 730. If, at the operation 731, it is determined that the bradycardia criterion of the operation 730 is met, then another operation 790 may be performed. Prior to the operation 790, according to an optional operation 788, the ambulatory patient 82 may be warned of the impending pacing. In particular, a speaker of the UI 280 may output a warning prompt prior to the planned pacing sequence of the pacing pulses of the operation 790 being caused to be delivered. According to an optional operation 789, the processor can be further configured to determine whether or not the cancel switch has been actuated after the warning prompt has been output. In such embodiments, the planned pacing sequence of the pacing pulses is not caused to be delivered responsive to determining that the cancel switch has been actuated after the warning prompt has been output.

Then, according to another operation 790, a pacing sequence may be delivered to the patient. An example is shown in the sample short pacing sequence 791, with pacing pulses 722, 723, 724, and which can be similar to the short pacing sequence 491 of FIG. 4. The pacing sequence 791 may be periodic or not, demand pacing or not. In particular, for the operation 790, the processor can be configured to cause at least some of the electrical charge provided by the source to be discharged via at least two of the therapy electrodes through the ambulatory patient so as to deliver to the ambulatory patient a planned pacing sequence of pacing pulses. The pacing pulses may have certain energies and successive ones of certain spacings between them. In this example, the certain spacings are indicated as PACP. At least some of the certain energies are at most 30 Joule. The pacing sequence is planned, in that it has certain energies, and timings, which define the spacings. The pacing sequence can further be planned by designating how many pacing pulses will be delivered, before stopping and looking.

The pacing pulses of the planned pacing sequence have waveforms. These waveforms can be monophasic, biphasic, and so on. In some embodiments, the waveforms are the same regardless of whether they are due to the bradycardia criterion being met, or the asystole criterion being met. For instance, at least one of the pacing pulses of the planned pacing sequence has a certain waveform when delivered responsive to the sensed ECG signal meeting the bradycardia criterion, and at least one of the pacing pulses of the planned pacing sequence can have the certain waveform when delivered responsive to the sensed ECG signal meeting the asystole criterion. Similarly, at least one of the pacing pulses of the planned pacing sequence can have the certain waveform when delivered after the defibrillation shock has been caused to be delivered per the operation 780.

If, at the operation 731, it is determined that the bradycardia criterion of the operation 730 is not met then, according to another operation 750, the sensed ECG signal 704 can be analyzed against an asystole criterion, to detect whether the patient is suffering from asystole. Asystole is commonly known as flatling, and corresponds to no electrical activity by the heart. The asystole criterion may be implemented in a number of ways, and can be distinct from the bradycardia criterion. In some embodiments, the asystole criterion includes detecting, in the ECG signal, no electrical activity that is larger than 200 micro Volt peak-to-peak. 100 micro Volt may be a good value. This detection can be for a suitable duration, such as at least 1.5 sec, at least 3 sec, at least 6 sec, perhaps 10 sec, and so on. For such detection noise may be removed, for example by cross-referencing to other channels, and so on.

According to another operation 751, it can be determined whether or not the asystole criterion is met at the operation 750. If, at the operation 751, it is determined that the asystole criterion of the operation 750 is met, then execution may proceed again to the operation 790, according to which the pacing sequence is delivered to the patient.

If, at the operation 751, it is determined that the asystole criterion of the operation 750 is not met then, according to another operation 780, a defibrillation shock 711 may be later delivered, in embodiments where a defibrillator is also provided, similarly with what was described for operation 480. It can be later, because some time may pass with other events, and optional other operations 770 may be performed in the interim, such as other diagnoses, prompts, and treatments.

Optionally, after operation 780, the operation 790 may be performed.

In some embodiments, a WMS paces the patient while concurrently monitoring for arrhythmias, and it may continue, adjust, or end the pacing in response to the monitoring. These arrhythmias may include different types of bradyarrhythmia and of tachyarrhythmia. An advantage is that, while external pacing can sometimes be pro-arrhythmic (in fact, if an intrinsic beat is not detected and a pacing pulse is applied on the T wave, then VF may be triggered), with the monitoring of embodiments, it can be detected if the patient has flipped into VF which, if left untreated, is lethal. Pacing is not effective during VF. A much larger defibrillation shock is necessary to terminate VF. This method is not guaranteed to sense every intrinsic beat that a patient may generate, but if there is a sustained rate recovery it will be detected. It is certainly better than open-loop pacing, which would provide no sensing capability at all. Examples are now described.

Figure 8:
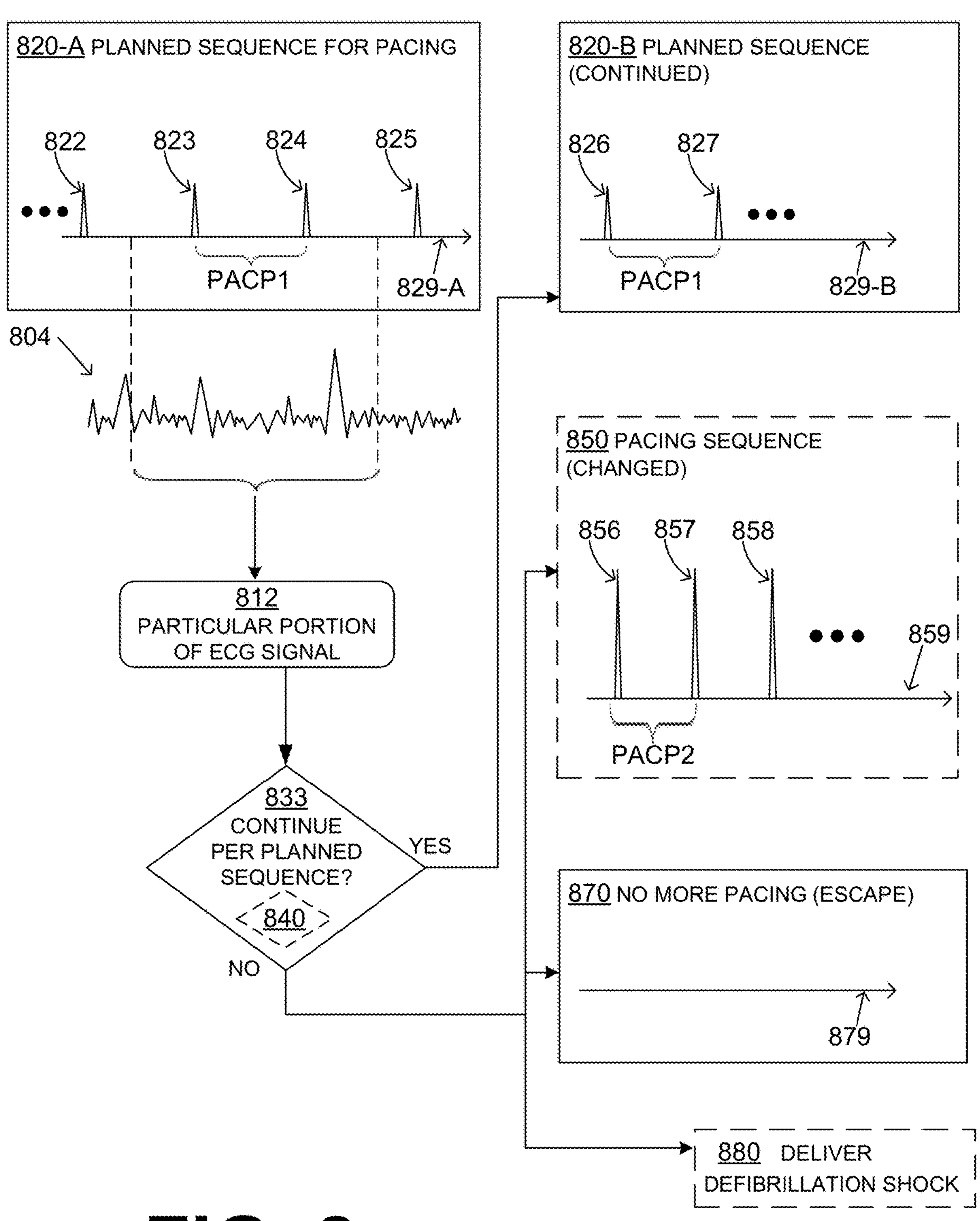
FIG. 8 shows a time diagram of a sample planned sequence for pacing and in which the ECG signal is detected concurrently with the pacing, and it further shows various possibilities of how the pacing may be continued per the planned sequence, or the sequence may be adjusted or stopped responsive to analyzing the detected ECG signal, according to embodiments.

FIG. 8 shows a number of elements. A sample planned sequence for pacing 820-A is shown as a time diagram. Sample pacing pulses . . . , 822, 823, 824, 825, which have started before pacing pulse 822, are shown against a time axis 829-A. In this example, the four sample pacing pulses 822, 823, 824, 825 are shown as occurring periodically, i.e., at regular intervals, with a spacing PACP1. And, since the spacing PACP1 is along a time axis, the spacing PACP1 is a time duration.

In FIG. 8 the four sample pacing pulses 822, 823, 824, 825 are shown as occurring periodically, but that is only for convenience of explanation and not necessary. In embodiments, a planned sequence 820-A need not be periodic, which means that the spacings between any two successive ones of these pacing pulses need not be identical. In some embodiments, at least some of the pacing pulses of the planned sequence can be delivered substantially periodically. For instance, in some embodiments, the planned sequence includes that the pacing pulses are delivered in successive groups that are separated by pauses. An example is now described.

Figure 9:
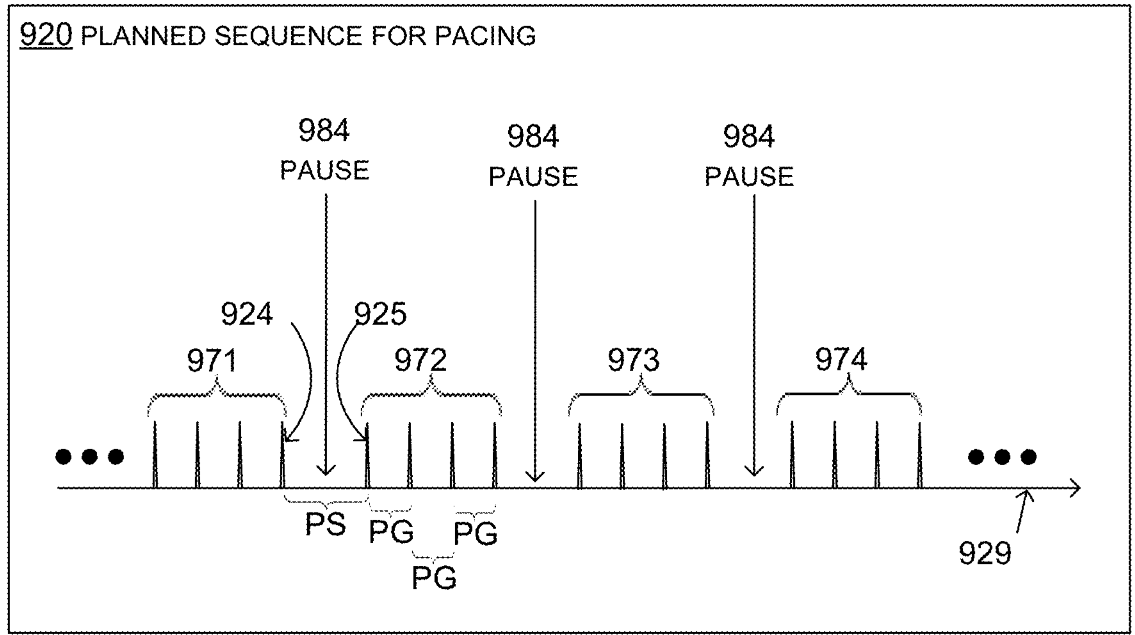
FIG. 9 is a time diagram of a sample planned pacing sequence that has groups of pacing pulses that are delivered substantially periodically, and in particular are delivered in groups of pulses that are separated by longer pauses, according to embodiments.

FIG. 9 shows a sample planned sequence for pacing 920. Sample groups . . . , 971, 972, 973, 974, . . . of pacing pulses are shown as a time diagram, plotted against a time axis 929. Within each of the groups 971, 972, 973, 974, the pacing pulses are actually periodic with a period PG, although that is not necessary either. Since they are periodic, these groups 971, 972, 973, 974 can also be called periodic groups.

Between these groups 971, 972, 973, 974 there are pauses 984, with period PG. For instance, the left-most shown of these pauses 984 is between a last one 924 of the pacing pulses in group 971, and a first one 925 of the pacing pulses in the next group 972. As will be seen later in this document, these pauses 984 are longer, meaning PS is larger than PG, to present a better opportunity to detect intrinsic heartbeats.

It will be further appreciated that the planned sequence 920 is itself periodic, if one considers that the repeating pattern includes one of the groups and its following pause.

In embodiments, pulses are delivered that do not have many interruptions. Or, the interruptions are minimized. For instance, a planned sequence may have at least 5 successive pacing pulses with four spacings between successive ones of them. At the same time, no two of the 5 successive pacing pulses have a spacing between them that is longer than 4 times an average of the four spacings. Or 3 times. Or 2 times. Or 1.7 times. Or 1.4 times. The smaller this number, the better the heart is covered with pacing. A brief periodic pause in pacing should not significantly impact pacing efficacy. One 5 second pause every 30 seconds still means that pacing pulses are delivered 83% of the time. One 5 second pause every 60 seconds would result in pacing pulses 92% of the time. Either one of these options is much better than having no pacing pulses at all. Having a higher pacing duty cycle would be preferable, but that needs to be weighed against the tradeoff of being able to see the patient's intrinsic rhythm less often.

For instance, in the example of FIG. 9, the following 5 successive pacing pulses may be considered: pulse 924 plus all of the pulses of group 972. Their four spacings are PS, PG, PG, PG. The average duration AVE_PER of these four spacings would be given by Equation 1.

$$AVE\_PER=[PS+PG+PG+PG]/4 \quad \text{Equation (1)}$$

And none of the spacings, for example the largest spacing PS would be longer than 4 times AVE_PER, or 3 times, or 2 times, or 1.7 times, or 1.4 times per the above. This Equation (1), and what it stands for, is shown with reference to the example of FIG. 9, but that is not necessary, and it can apply to other planned sequences 820-A. If PS=2×PG, then the pattern is to simply skip a pacing pulse.

Returning to FIG. 8, a sample ECG signal 804 is shown, along the time axis 829-A of the planned sequence 820-A. Specifically, a particular portion 812 of the ECG signal 804 has been sensed after the delivery per the planned sequence starts, and before it stops. As applied to this example, this means that the particular portion 812 has been sensed after the pacing pulse 822 has been delivered, and before the pacing pulse 825 has been delivered.

FIG. 8 thus shows how particular portion 812 of the ECG signal 804 is detected concurrently with the pacing of the planned sequence 820-A. The particular portion 812 is then analyzed and, according to a decision diamond 833, a continuance determination is made of whether or not to continue pacing according to the planned sequence 820-A.

Regarding the analyzing of the ECG signal, in some embodiments it is attempted to detect all heartbeats, in order to determine how successful the pacing is in: a) capturing the heart in the first place and, hopefully in b) eliciting intrinsic heartbeats. In other embodiments, or at other times, only intrinsic heartbeats are detected by a special detection technique that is now described.

Figure 10:
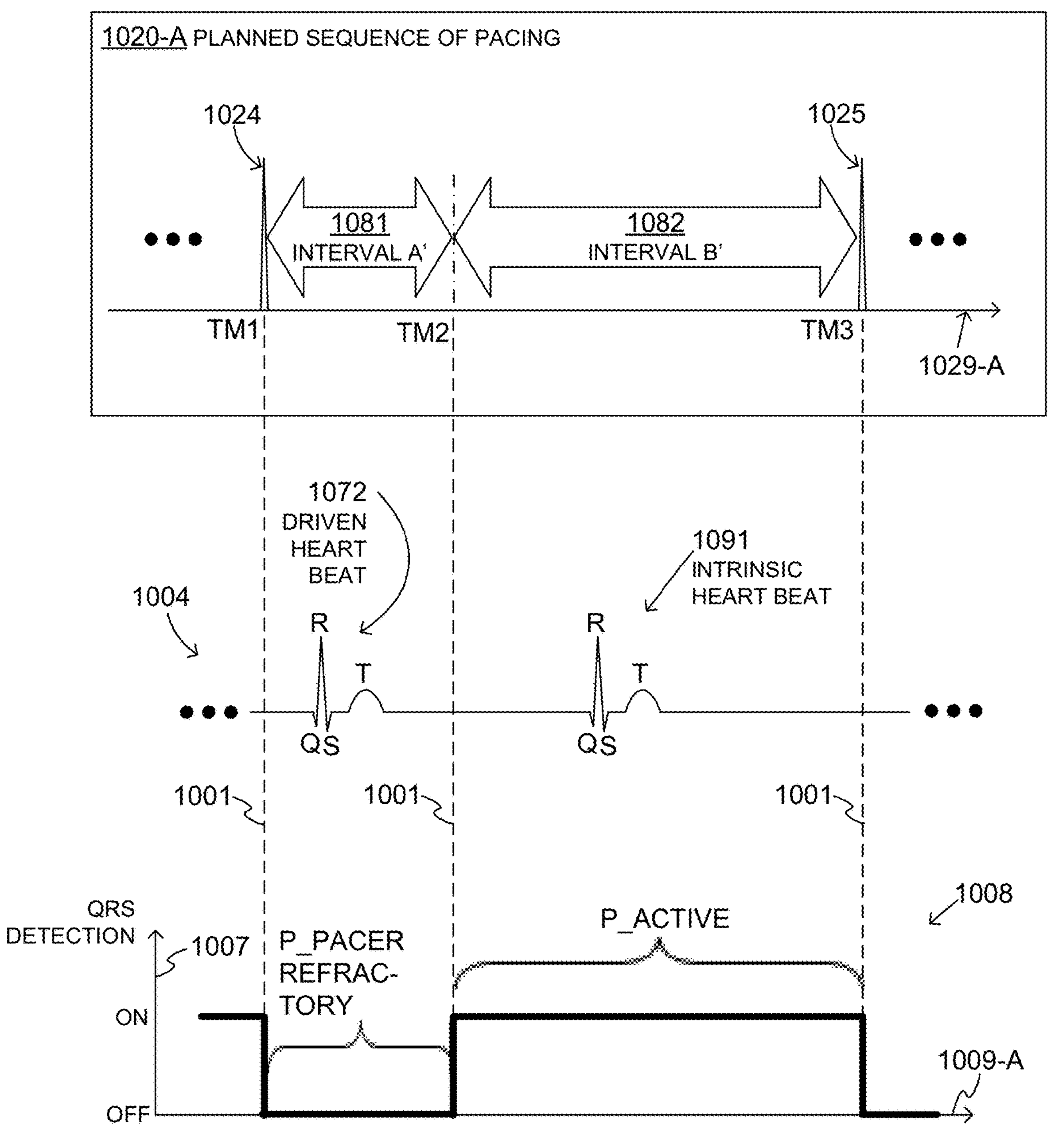
FIG. 10 shows elements of a technique for detecting intrinsic heartbeats but excluding heartbeats driven by the pacing according to embodiments.

FIG. 10 shows a planned sequence 1020-A against a time axis 1029-A. The planned sequence 1020-A includes pacing pulses . . . , 1024, 1025, . . . . The pacing pulse 1024 occurs at a time TM1 and the pacing pulse 1025 occurs at a time TM3. The pacing pulses 1024, 1025 could be any two successive pulses of the previously described sequences 820-A or 920. In fact, they could be the pulses 924, 925, in which case the time distance, or spacing, between TM1 and TM3 would be PS.

A time TM2 divides the spacing between the two pacing pulses 1024, 1025 into an Interval A' 1081 and Interval B' 1082. An idealized ECG signal 1004 shows two different types of detected heartbeats.

In this example, during Interval A' 1081, a heartbeat 1072 occurs, and is considered to be a driven heartbeat. It is driven, in the sense that it was caused to happen by the pacing pulse 1024. This could be part of demand pacing. A heartbeat might not always be caused to happen by a pacing pulse. Even if the heartbeat 1072 occurs, it may not be detected. And, even if the heartbeat 1072 could be detected, it is not always detected. In some embodiments, detection of the driven heartbeat is not performed; rather, the delivery of the pacing pulse 1024 is assumed to capture the heart and detection during the interval 1081 is not required. The pacing pulse 1024 defines the beginning of the interval 1082 at TM2, at which point detection starts.

In this example, during Interval B' 1082, a heartbeat 1091 is detected, and is considered to be an intrinsic heartbeat. It is intrinsic, in the sense that it was not directly caused by the pacing pulse 1024, as was the driven heartbeat 1072. Rather, the heart by itself generated this intrinsic heartbeat 1091, perhaps due to its conditioning from previous pacing. An intrinsic heartbeat might not always be detected. Detecting an intrinsic heart beat may inhibit pace pulse delivery, as known for demand pacing operations.

In some embodiments, detection techniques involve turning off and on the QRS detection. This may involve turning ON and OFF a QRS detector, or alternate between considering the output of a QRS detector and disregarding or ignoring that output. Such alternating QRS detection is shown in a time diagram 1008. A vertical axis 1007 has ON and OFF values, and is perpendicular to a time axis 1009-A. The time axis 1009-A runs concurrently with the time axis 1029-A, as shown by the long perpendicular lines 1001.

For purposes of running QRS detection, intervals are now defined. The Interval B' 1082 can be thought of as an active period that starts after one of the pacing pulses 1024 is delivered, meaning after time TM1, and ends in conjunction with the next one of the pacing pulses 1025 being delivered, meaning in conjunction with time TM3. Here, "in conjunction" means that the end of the Interval B' 1082 is planned that way, and could be somewhat before the time TM3, or right on the time TM3, and so on. The QRS detector can be ON for the active period P_ACTIVE.

The Interval A' 1081 can be thought of as a pacer refractory period that starts in conjunction with the one of the pacing pulses 1024 being delivered, meaning in conjunction with time TM1, and ends when the above-described active period starts, meaning at time TM2. This pacer refractory period can be complementary to the active period. Here, "in conjunction" means that the start of the Interval A' 1081 is planned that way, and could be somewhat after the time TM1, or right on the time TM1, and so on. The QRS detection can be OFF for the pacer refractory period P_PACER REFRACTORY. The pacer refractory period of embodiments should not be confused with the refractory period exhibited by ECG pulses. Indeed, the heart is refractory to any stimulation following a QRS. For purposes of pacer embodiments, however, a pacer refractory period may occur immediately after a sensed beat or a pacing pulse. A pacer refractory period can be a "logical" period when any detected R-wave or P-wave is ignored. This should also not be confused with a blanking period; a blanking period is a time, nominally shorter than a pacer refractory period, where circuitry is disabled/blanked to minimize the interference from the actual pacing pulse.

In embodiments, the pacer refractory period of the QRS detector is coordinated with the heart's refractory period. The T-wave of a driven complex may extend 400-500 msec after the pacing pulse. In some instances, therefore, the pacer refractory period, and time TM2, may need to be at least 500 msec after time TM1 to avoid detecting driven complexes.

Therefore, in some embodiments, analyzing the ECG signal may include detecting QRS complexes in the particular portion of the ECG signal during the active period P_ACTIVE, but not in the pacer refractory period P_PACER REFRACTORY. This way, in some embodiments, the continuance determination of the decision diamond 833 can optionally be made from the QRS complexes detected in the active period.

Returning again to FIG. 8, possible results of the decision diamond 833 are now described. In some embodiments, the decision can be YES. For instance, according to an optional internal decision diamond 840, it may be determined whether one or more criteria for change are met and, if not, then the decision YES of the diamond 833 can be a default one.

If the decision at the diamond 833 is to continue, the result is shown in the sample planned sequence 820-B, which is meant to be a continuation of the sample planned sequence 820-A. In particular, the planned sequence 820-B shows sample pacing pulses 826, 827, . . . against a time axis 829-B. These pacing pulses 826, 827, . . . occur periodically, at the same regular intervals with spacings PACP1 as the pacing pulses in FIG. 820-A.

The continuing can be performed with no interruption to the planned sequence, or with a short interruption, e.g., where the time axis 829-A ends. For instance, the last planned pacing pulse 825 might not be caused to be delivered, and so on.

If the decision at the diamond 833 is to not continue, there can be a number of options, pointed to by multiple arrows.

One of the options is that pacing will continue, but the planned sequence will change—will be replaced with an updated sequence. In such instances, upon the discontinuing, the processor may start causing at least some of the electrical charge provided by the source to be discharged via at least two of the therapy electrodes through the ambulatory patient so as to continue delivering to the ambulatory patient an updated sequence of pacing pulses.

Such a result is shown in the sample changed or updated sequence 850, which is meant to continue after the planned sequence 820-A. In particular, the updated sequence 850 shows sample pacing pulses 856, 857, 858, . . . against a time axis 859. These pacing pulses 856, 857, 858 can be updated from those of the planned sequence in a number of ways.

In some embodiments, these pacing pulses 856, 857, 858, . . . are updated in that they have at least 10% more energy than the pacing pulses of the planned sequence 820-A. In this example, the updated pulses of sequence 850 are shown taller, to indicate that they have more energy.

In some embodiments, the pacing pulses of the planned sequence 820-A have a first average period—here PACP1—and at least four of the pacing pulses in the updated sequence 850 (of which only three are shown) have a second average period at least 10% different than the first average period. In this example, the updated pulses occur faster, with a shorter sample period PACP2. In other instances, the more successful the pacing is, the pacing period may get longer—in other words slow down the pacing to allow more and more intrinsic heartbeats to be detected.

The updated sequence 850 may be implemented if an inadequacy criterion is used, with which to determine the adequacy or not of the planned pacing sequence. For instance, the continuance determination may include determining whether or not an inadequacy criterion is met, and the discontinuing may be performed responsive to determining that the inadequacy criterion is met, and where the discontinuing would be followed by the updated pacing 850. The inadequacy criterion may include that intrinsic heartbeats do not occur, and/or driven heartbeats do not occur, and so on.

Again, the continuing with the updated sequence 850 can be performed with no interruption to the planned sequence, or with a short interruption, e.g., where the time axis 829-A ends. For instance, the last planned pacing pulse 825 might not be caused to be delivered, and so on.

Another one of the options is to stop pacing altogether. In such embodiments, the discontinuing may include causing no more of the pacing pulses to be delivered for at least two minutes. Such a result is shown in the sample box 870. While a time axis 879 is shown, no pacing pulses are caused to be delivered.

This option of stopping pacing altogether may be implemented in a number of ways. In some embodiments, the continuance determination of the decision diamond 833 includes determining whether or not an escape criterion is met, and the discontinuing is performed responsive to determining that the escape criterion is met. In some embodiments, the processor is further configured to detect QRS complexes in the particular portion 812 of the ECG signal, and to compute a heart rate from the detected QRS complexes. In such embodiments, the escape criterion may include that the heart rate is larger than 30 beats per minute (bpm). In some of those embodiments, the QRS complexes have been detected during only the active period but not during the pacer refractory period of FIG. 10. In such embodiments, one of the pacing pulses in the planned sequence may be prevented from being delivered, responsive to detecting an intrinsic QRS complex. This way, if intrinsic QRS complexes take over, pacing may stop altogether. This is possible in embodiments thanks to the pauses. Otherwise, with fast pacing, the heart would have to beat even faster for escaping pacing. This would probably not be good for a WMS patient because a WMS pacing is desirable mostly if the patient's rate is too low to sustain life.

One more option is that the WMS may defibrillate per the operation 880, in embodiments where a defibrillator is also provided. The operation 880 may be performed, for instance, from the diamond 833 if a defibrillation criterion is met at the optional internal diamond 840. This may be in addition to defibrillating again later anyway. Other events, detections, etc. may or may not intervene.

Figure 11:
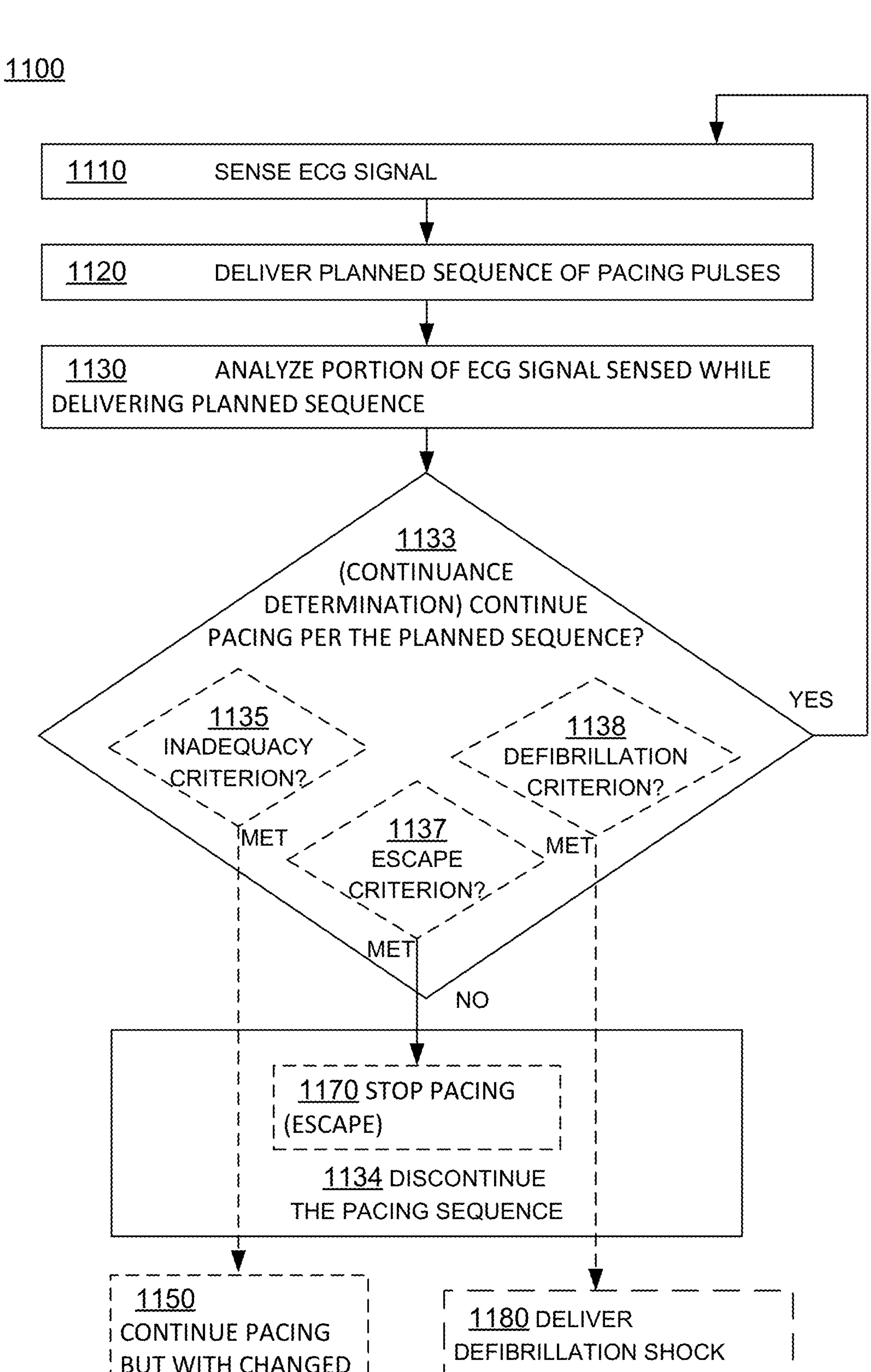
FIG. 11 is a flowchart for illustrating sample methods according to embodiments.

FIG. 11 shows a flowchart 1100 for describing methods according to embodiments. The method can start at an operation 1110, where an ECG signal is sensed. This can be performed as described above.

According to another operation 1120, a planned sequence of pacing pulses can be caused to be delivered. In particular, at least some of the electrical charge provided by the source can be caused to be discharged via at least two of the therapy electrodes through the ambulatory patient so as to deliver to the ambulatory patient a planned sequence of pacing pulses. The planned sequence can be as described above. Plus, it may have at least 5 successive pacing pulses with four spacings between successive ones of them, no two of the at least 5 successive pacing pulses having a spacing between them that is longer than 4 times an average of the four spacings. Or 3 times, or 2 times, or 1.7 times or 1.4 times, as per the above. Optionally, and similarly to what was described previously, the ambulatory patient may be warned of the impending pacing prior to the operation 1120. In particular, a speaker of the UI 280 may output a warning prompt prior to the planned sequence of the pacing pulses of the operation 1120 being caused to be delivered. The processor can be further configured to determine whether or not the cancel switch has been actuated after the warning prompt has been output. In such embodiments, the planned sequence of the pacing pulses is not caused to be delivered responsive to determining that the cancel switch has been actuated after the warning prompt has been output.

According to another operation 1130, a particular portion of the ECG signal, which has been sensed after the delivery per the planned sequence starts and before it stops, may be analyzed. A conventional rhythm analysis with a very high sensitivity can be run, precluding the possibility that the patient may have undetected VF. In embodiments, simultaneous, multi-channel, real-time R-wave detection across all ECG channels that meet one or more criteria for minimal noise and continuous electrode contact may be used. Once the detector refractory period is satisfied, an R-wave detection on any qualified ECG channel is considered an intrinsic beat for the purpose of inhibition. Moreover, the QRS detection may be turned off and on for each ECG channel's R-wave detector. Additionally, sensing refractory periods can be configurable, and thus allow refractory periods for intrinsic pulses to be different from refractory periods following pacing pulse delivery. Also, if a high number of paced heartbeats are occurring, consider the patient's rhythm to be bradycardic/asystolic since few or no intrinsic R-waves are being detected by the sensitive, multi-channel R-wave detectors during the long periods between pacing pulses (e.g., 1.5 sec at 40 bpm). If there are long periods of time without paced heartbeats (e.g., more than 3 sec implying at least 2 intrinsic R-waves have been detected), perform rhythm analysis on these pace-pulse-free ECG data sections.

According to another operation 1133, a continuance determination may be made from the analyzed particular portion of the ECG signal. Similarly with what was written for the decision diamond 833, the continuance determination may be as to whether or not to continue pacing according to the planned sequence.

If, at the operation 1133, the answer is yes, then causing at least some of the electrical charge provided by the source to be discharged via at least two of the therapy electrodes through the ambulatory patient may be continued, so as to deliver to the ambulatory patient the planned sequence of pacing pulses for at least 10 more pacing pulses. That would be by the execution returning to operation 1110, and then 1120 for continuing the planned sequence.

If, at the operation 1133, the answer is no, then according to another operation 1134 the causing to be delivered to the ambulatory patient the planned sequence of pacing pulses may be discontinued.

If at the operation 1133 an inadequacy criterion 1135 is met then, according to another, optional operation 1150, pacing may be continued, but with different energy and/or with different average period, similarly with what was described above for the updated sequence 850.

A method of external pacing is to give a pacing pulse after refractory period of intrinsic QRS complex and then wait an interval equal to the intrinsic rate. If an intrinsic QRS complex is detected about the same intrinsic rate from the previous QRS complex, the pacing is not captured and increase the energy level then repeat the same previous procedure until the pacing is captured.

When a pacing pulse is captured, the interval from the pacing pulse to the following intrinsic QRS complex should be significantly longer than the previous pacing pulse which failed to capture to the intrinsic QRS complex.

Once the pacing threshold becomes known, the pacing level can be set at twice the pacing threshold and the above-mentioned methods can be applied.

The operation 1134 includes the optional operation 1170, where pacing may stop altogether for at least two minutes. That may be where an escape criterion 1137 is met, and so on, per the above.

If at the operation 1133 a defibrillation criterion 1138 is met then, according to another operation 1180, a defibrillation shock may be caused to be delivered, in embodiments where a defibrillator is also provided.

Another method of external pacing would be to apply pacing pulses and examine the ECG signal to detect the presence of artifacts. If the ECG is determined to be artifact-free, then intrinsic beats (QRS complexes) can be detected between pacing pulses. If excessive artifacts are detected, then pauses can be applied as described above to allow artifact-free analysis. In this scenario it is important that the QRS detector have a pacer refractory period after the pacing pulse to prevent detection of the pacing pulse or the driven complex. This method may work best with a relatively low pacing pulse rate, perhaps 60 bpm. At 60 bpm a 500 msec pacer refractory period can be applied and the remaining 500 msec could be used for sensing intrinsic complexes.

On the other hand, if the pacing rate is set to 90 bpm, then the interval between pacing pulses is only 666 mS. If 500 msec us used for a pacer refractory period, then only 166 msec are available for sensing intrinsic complexes. That means that intrinsic complexes can be detected only about 25% of the time, which is not good if the pacing pulses have not achieved capture. If the patient's rate is the same (or similar) to the pacing rate, it is possible that all of the intrinsic beats could fall in the pacer refractory period and the intrinsic rate is never detected.

In some embodiments the refractory period could be different for different patients, and the pacer refractory period may be set accordingly. It is possible that a physician could set the pacer refractory period when the device is prescribed, or perhaps the device could sense the end of the driven complex and start looking for intrinsic complexes at the end of the driven T-wave.

In the methods described above, each operation can be performed as an affirmative act or operation of doing, or causing to happen, what is written that can take place. Such doing or causing to happen can be by the whole system or device, or just one or more components of it. It will be recognized that the methods and the operations may be implemented in a number of ways, including using systems, devices and implementations described above. In addition, the order of operations is not constrained to what is shown, and different orders may be possible according to different embodiments. Examples of such alternate orderings may include overlapping, interleaved, interrupted, reordered, incremental, preparatory, supplemental, simultaneous, reverse, or other variant orderings, unless context dictates otherwise. Moreover, in certain embodiments, new operations may be added, or individual operations may be modified or deleted. The added operations can be, for example, from what is mentioned while primarily describing a different system, apparatus, device or method.

A person skilled in the art will be able to practice the present invention in view of this description, which is to be taken as a whole. Details have been included to provide a thorough understanding. In other instances, well-known aspects have not been described, in order to not obscure unnecessarily this description.

Some technologies or techniques described in this document may be known. Even then, however, it does not necessarily follow that it is known to apply such technologies or techniques as described in this document, or for the purposes described in this document.

This description includes one or more examples, but this fact does not limit how the invention may be practiced. Indeed, examples, instances, versions or embodiments of the invention may be practiced according to what is described, or yet differently, and also in conjunction with other present or future technologies. Other such embodiments include combinations and sub-combinations of features described herein, including for example, embodiments that are equivalent to the following: providing or applying a feature in a different order than in a described embodiment; extracting an individual feature from one embodiment and inserting such feature into another embodiment; removing one or more features from an embodiment; or both removing a feature from an embodiment and adding a feature extracted from another embodiment, while providing the features incorporated in such combinations and sub-combinations.

In general, the present disclosure reflects preferred embodiments of the invention. The attentive reader will note, however, that some aspects of the disclosed embodiments extend beyond the scope of the claims. To the respect that the disclosed embodiments indeed extend beyond the scope of the claims, the disclosed embodiments are to be considered supplementary background information and do not constitute definitions of the claimed invention.

In this document, the phrases "constructed to", "adapted to" and/or "configured to" denote one or more actual states of construction, adaptation and/or configuration that is fundamentally tied to physical characteristics of the element or feature preceding these phrases and, as such, reach well beyond merely describing an intended use. Any such elements or features can be implemented in a number of ways, as will be apparent to a person skilled in the art after reviewing the present disclosure, beyond any examples shown in this document.

Incorporation by reference: References and citations to other documents, such as patents, patent applications, patent publications, journals, books, papers, web contents, have been made throughout this disclosure. All such documents are hereby incorporated herein by reference in their entirety for all purposes.

Parent patent applications: Any and all parent, grandparent, great-grandparent, etc. patent applications, whether mentioned in this document or in an Application Data Sheet ("ADS") of this patent application, are hereby incorporated by reference herein as originally disclosed, including any priority claims made in those applications and any material incorporated by reference, to the extent such subject matter is not inconsistent herewith.

Reference numerals: In this description a single reference numeral may be used consistently to denote a single item, aspect, component, or process. Moreover, a further effort may have been made in the preparation of this description to use similar though not identical reference numerals to denote other versions or embodiments of an item, aspect, component or process that are identical or at least similar or related. Where made, such a further effort was not required, but was nevertheless made gratuitously so as to accelerate comprehension by the reader. Even where made in this document, such a further effort might not have been made completely consistently for all of the versions or embodiments that are made possible by this description. Accordingly, the description controls in defining an item, aspect, component or process, rather than its reference numeral. Any similarity in reference numerals may be used to infer a similarity in the text, but not to confuse aspects where the text or other context indicates otherwise.

The claims of this document define certain combinations and subcombinations of elements, features and acts or operations, which are regarded as novel and non-obvious. The claims also include elements, features and acts or operations that are equivalent to what is explicitly mentioned. Additional claims for other such combinations and subcombinations may be presented in this or a related document. These claims are intended to encompass within their scope all changes and modifications that are within the true spirit and scope of the subject matter described herein. The terms used herein, including in the claims, are generally intended as "open" terms. For example, the term "including" should be interpreted as "including but not limited to," the term "having" should be interpreted as "having at least," etc. If a specific number is ascribed to a claim recitation, this number is a minimum but not a maximum unless stated otherwise. For example, where a claim recites "a" component or "an" item, it means that the claim can have one or more of this component or this item.

In construing the claims of this document, the inventor(s) invoke 35 U.S.C. § 112(f) only when the words "means for" or "steps for" are expressly used in the claims. Accordingly, if these words are not used in a claim, then that claim is not intended to be construed by the inventor(s) in accordance with 35 U.S.C. § 112(f).

Having fully described various embodiments of the present disclosure and the claimed subject matter some additional details are provided. Prior to turning to some additional details, some additional scenarios are described utilizing various embodiments of the claimed subject matter.

In one non-limiting scenario, a person may have a heart condition, where the heart of the person may be monitored and therapy applied as needed. Accordingly, a wearable medical device (WMD) may be utilized. For example, the WMD may include a wearable cardioverter defibrillator (WCD) that may be utilized by the person. Briefly, the WCD may include a support structure such as, but not limited to, a wearable garment (e.g., a vest) as described above. Accordingly, the vest may include a number of electrodes. As described in previous examples, the vest may include two therapy electrodes that may be configured to provide therapy to the heart of the person. Additionally, the vest may include one or more monitor electrodes (monitor electrodes), where the monitor electrodes may be configured to receive electrical signals from the activity of the heart (e.g., ECG signal). The WCD may include a WCD monitor, which may include various electronic components for functionality of the WCD. The WCD monitor may be communicatively coupled with the electrodes (e.g., therapy electrodes and the monitor electrodes). Additionally, the WCD monitor may include a processor, an electrical energy storage device (e.g., battery), and a WCD pacing module, where the WCD pacing module may be configured to facilitate the activities as described herein (i.e., the WCD pacing module may be configured to determine if the ECG signal meets one or more cardiac pacing criteria). For example, the WCD pacing module may be implemented in software using the hardware already present in the WCD for delivering defibrillation shocks. In other scenarios, the WCD pacing module may be implemented as a hardware module configured to deliver pacing pulses that is in addition to or in combination with the hardware already present in a WCD for delivering defibrillation shocks. In yet other scenarios, the WCD pacing module, in its various forms, may be included in a processor or one or more processors to facilitate at least some of the functionality described herein. As used in this context, the WCD pacing module being in a processor or one or more processors can refer to embodiments in which software loaded in a memory of the WCD or a remote location is to be executed by the processor or one or more processors which may be in the WCD monitor or distributed across other components of the WCD system.

Prior to describing in further detail the claimed subject matter, further detail regarding pacing utilizing electrical signals may be provided. Even though the pacing pulses described above are in terms of energy, those skilled in the art of pacers will appreciate that in various alternative examples, the pacing pulses may be defined in terms of current as is well known (e.g., see Doukky R, Bargout R, Kelly R F, Calvin J E. Using transcutaneous cardiac pacing to best advantage: How to ensure successful capture and avoid complications. J Crit Illn. 2003 May; 18(5):219-225. PMID: 30774278; PMCID: PMC6376978. https://www.ncbi.nlm.gov/pmc/articles/PMC6376978/). For example, in some embodiments the pacing pulses can be delivered using current source circuitry as is disclosed in U.S. Pat. No. 6,751,501B1 "Method and apparatus for myocardial control" filed Jan. 14, 2000.

In the non-limiting scenario, the person may be wearing the WCD and performing normal daily activities. The monitor electrodes may continually receive ECG signals from the heart, where the received ECG signals may be processed for various information by the WCD pacing module. The WCD pacing module may include a software module that may be implemented by the processor as described. In this example, the person may experience a heart related event such as, but not limited to, a bradycardia event. In this example, the WCD pacing module may determine that the received ECG signal indicates the bradycardia event, which may be one of several cardiac pacing criteria capable of being determined by the WCD pacing module.

Responsive to determining that the received ECG signal indicates the bradycardia event, WCD pacing module may cause a warning to be communicated, where the warning may be configured to communicate that pacing will be performed by the WCD. The warning may be communicated by a variety of methods such as, but not limited to, an audio and/or visual methods. In one example, the WCD pacing module may be configured to activate a speaker to sound the warning (e.g., a voice stating "warning, pacing will commence", an alert sound, etc.). In another example, the WCD pacing module may be configured to activate a light located on the WCD. In yet another example, the WCD pacing module may be configured to cause the WCD to display a warning on a user interface included in the WCD. Once the WCD has provided the warning, the WCD may be configured to provide electrical energy as cardiac pacing pulses to the therapy electrodes for cardiac pacing of the heart. This would result in the transcutaneous pacing of the heart (i.e., through the skin). Once the pacing has commenced, in some examples, the WCD pacing module may cause to communicate a warning that pacing is in process (e.g., pacing active warning).

In one example, prior to commencing the cardiac pacing, the WCD pacing module may be configured to receive an indication to not cardiac pacing. Responsive to the received indication, the WCD pacing module may be configured to not provide electrical energy (e.g., prevent cardiac pacing). The indication may be provided by various interfaces such as, but not limited to, a user interface (e.g., graphical user interface), a button that may be configured to actuated, a verbal command that may be received via a microphone and processed by the processor, or so forth.

In another example, while the cardiac pacing is occurring, the WCD pacing module may be configured to receive an indication to stop the cardiac pacing. Responsive to the received indication, the WCD pacing module may be configured to stop providing electrical energy (e.g., stop cardiac pacing). The indication to stop cardiac pacing may be received while the WCD is providing the pacing active warning. The indication may be provided by various interfaces such as, but not limited to, a user interface (e.g., graphical user interface), a button that may be configured to actuated, a verbal command that may be received via a microphone and processed by the processor, or so forth.

The indication may be provided by various interfaces such as, but not limited to, a user interface, a button that may be actuated, a verbal command that may be received via a microphone and processed by the processor, or so forth.

In another scenario, the WCD may include a response mechanism by which a person (i.e., the person wearing the WCD and/or a bystander) may respond to the warning. For example, the WCD may include a button either mounted on the support structure or on the WCD monitor. Activating the button may cause the WCD to prevent the cardiac pacing. As may be appreciated, transcutaneous pacing may involve stimulating the skeletal muscles along with the cardiac muscles, which may cause discomfort. Accordingly, if the person was experiencing a bradycardia event that may not necessarily need pacing (i.e., the person is fully conscious and not experiencing other symptoms such as, low oxygen, light headedness, losing consciousness, etc.), the person may be provided the ability to prevent the cardiac pacing by the WCD. However, if the bradycardia event falls below certain threshold(s) (e.g., below 20 bpm), the person may be losing or has lost consciousness, where the pacing by the WCD may provide life sustaining therapy.

In another scenario, the WCD pacing module may determine that the received ECG signal may meet one or more asystole pacing criteria (i.e., cardiac arrest with little or no ECG signal). Responsive to determining that the person meets one or more asystole pacing criteria, the WCD pacing module may provide the warning that the pacing will be performed by the WCD. The warning may facilitate providing an opportunity to confirm that the person is experiencing an asystole event because there may be a possibility that the monitor electrodes may have detached from the skin of the person and/or disconnected from the WCD. However, if after the warning, the WCD pacing module does not receive a response, the WCD may proceed to cardiac pace the heart via the therapy electrodes. As may be appreciated, if one or more asystole pacing criteria is met, it is highly likely that the person has lost consciousness due to the non-activity of the heart.

In the event that the WCD does pacing, the electrical energy provided as cardiac pacing pulses to the therapy electrodes may be provided as electrical current (e.g., 70 mA) to facilitate a cardiac pacing of 70 bpm or any range between 20 bpm and 90 bpm.

In another scenario, the WCD pacing module may determine if the received ECG signal meets one or more cardiac shock criteria. Responsive to determining that the received ECG signal meets the one or more cardiac shock criteria, the WCD pacing module may cause the WCD to provide a cardiac shock to the therapy electrodes.

In another scenario, the WCD pacing module may be configured to detect an indication of cardiopulmonary resuscitation (CPR). For example, the person may have experienced a bradycardia event and may have lost consciousness. The WCD pacing module may have determined that the ECG signal meets one or more bradycardia pacing criteria and provided the warning. A bystander or an emergency personnel may have seen the person experiencing the cardiac event and started CPR. In this scenario, prior to providing the cardiac pacing, the WCD pacing module may detect that CPR is being performed. In response, the WCD pacing module may be configured to take a predetermined actions such as, for example, terminate initiation of cardiac pacing activity; cause the WCD to issue a warning to bystanders stay away from the patient while pacing pulses are being delivered, etc.

In one example, the WCD pacing module may be capable of detecting CPR being performed by measurements of impedance. For example, the WCD monitor may include components to receive and process impedance utilizing the monitor electrodes. Accordingly, the WCD pacing module may be configured to determine changes in impedance between the monitor electrodes due to the movement of the chest from CPR being performed. In another example, the WCD pacing module may be capable of detecting CPR being performed by receiving information from a sensor such as, but not limited to, an accelerometer or pressure sensor, which may be included in the support structure.

Continuing with the scenario of the WCD pacing module, upon determining that CPR is being performed, the WCD pacing module may provide guidance. For example, the WCD pacing module may be configured to provide an audible pacing instruction to the person performing the CPR (e.g., a beep sound similar to a metronome, verbal commands "compress chest . . . compress chest", etc.). Alternatively, the WCD pacing module may be configured to provide a visual pacing instruction to the person performing the CPR (e.g., a light, graphical visual indications on a user interface, etc.).

In another example, the WCD pacing module may be capable of determining the rate of the CPR being performed (i.e., chest compressions per minute). In this example, the WCD pacing module may be able to facilitate adjustment of the CPR (i.e., increase or decrease the rate of chest compressions). The adjustment may be facilitated by sound and/or by visual indications (e.g., beep, verbal, light, user interface, etc.).

In another scenario, the WCD pacing monitor may have determined that one or more cardiac pacing criteria was met. The WCD pacing monitor may have caused the WCD to commence cardiac pacing. However, in some embodiments the WCD may include a proximity sensor used by the WCD pacing monitor to detect a proximity of a bystander. Upon detection of the bystander, the WCD pacing monitor may cause the WCD to provide verbal commands such as, but not limited to, requesting the bystander to perform CPR, call emergency (e.g., 911), and so forth.

As mentioned previously, some bradycardia events may not require therapy (e.g., cardiac pacing, shock, etc.). The WCD may include sensors that may facilitate determination of a posture of the person. For example, the WCD pacing module may determine that the ECG signal meets one or more pacing criteria. However, one or more sensors included in the support structure and/or the WCD monitor may facilitate determination of the posture of the person by the WCD pacing module. If it is determined that the person is not lying down (e.g., standing, sitting up, etc.), the WCD pacing module may terminate initiation of cardiac pacing. In one example, the WCD pacing module may terminate initiation of cardiac pacing even if no response was received subsequent to the warning of cardiac pacing because the person is standing (i.e., no symptom of life threatening bradycardia).

As may be appreciated after review of the present disclosure, the WCD pacing module may be capable of a variety of responses to received inputs. Accordingly, the WCD pacing module may be adapted to responding to a change in the condition of the person. In one example scenario, the WCD may be providing cardiac pacing to the person, who suffered a cardiac event. The cardiac pacing may have brought the person back to consciousness. The person may have regained enough consciousness to actively terminate the cardiac pacing. However, in one example, the WCD pacing module may be capable of detecting, via one or more sensors of the WCD, that the person has regained consciousness (e.g., one or more of a motion sensor indicating the person is self-moving, ECG signal indicating non-bradycardia, accelerometer indicating a change in posture, etc.). Responsive to detecting that the person has regained consciousness, the WCD pacing module may cause the WCD to terminate the cardiac pacing.

In another example scenario, while the WCD may be providing cardiac pacing, the WCD pacing module may detect a bystander as described above for a previous scenario. The WCD pacing module may cause the WCD to instruct the bystander to perform CPR, which may include instructions on how to perform CPR. The WCD pacing module may be capable of detecting an acknowledgment from the bystander that they will perform CPR (e.g., via a user interface, verbal acknowledgment via a microphone, a button/switch on the WCD monitor, etc.). In this scenario, responsive to receiving the acknowledgement, the WCD pacing module may cause the WCD to terminate the cardiac pacing.

In yet another example scenario, the WCD pacing module may be capable of performing a confirmation prior to cardiac pacing. For example, the WCD pacing module may have received an ECG signal that may meet one or more pacing criteria (e.g., bradycardia or asystole). In one example, the WCD pacing module may analyze other portions of the ECG signal to confirm one or more pacing criteria being met. In another example, the WCD pacing module may analyze a subsequently received ECG signal to confirm one or more pacing criteria continues being met. Once confirmed, the WCD pacing module may proceed to cause the warning. As may be appreciated in light of the present disclosure, the WCD pacing module may be capable of confirming that the person needs cardiac pacing prior to initiating cardiac pacing activities by the WCD.

Prior to initiating cardiac pacing, the WCD pacing module may cause the WCD to stabilize and/or augment the interface between the therapy electrodes and the skin of the person. For example, prior to initiating cardiac pacing, the WCD pacing module may be configured to cause the WCD to deploy electrolyte material (e.g., electrolyte gel). The deployment of electrolyte gel at the interface may facilitate a stable electrical interface for transcutaneous cardiac pacing. Additionally, the WCD pacing module may be capable of determining the stability of the electrical interface during cardiac pacing by the WCD. Accordingly, the WCD pacing module may be capable of periodically and/or continuously causing to deploy electrolyte material.

In yet another example scenario, the WCD pacing module may be capable of moderating some negative effects of transcutaneous pacing. For example, the WCD pacing module may be configured to cause the WCD to provide cardiac pacing the heart using an algorithm that may provide an alternating pattern of utilizing the therapy electrodes. The alternating pattern may include alternating electrical polarity of the therapy electrodes to help alleviate potential electrolysis of a gel, which the WCD may disperse at the interface between the electrode and the skin of the person just prior to delivering pacing pulses. The electrolysis of the gel at the interface may cause injury to the skin. Accordingly, alternating electrical polarity of the therapy electrodes during cardiac pacing may alleviate the potential for injury of the skin.

It should be appreciated that "criteria" as used herein may refer to at least one criterion depending upon the context. Accordingly, the claimed subject matter is not limited in this respect.

Having fully described some various non-limiting example scenarios and various embodiments, further figures are described below.

Figure 12:
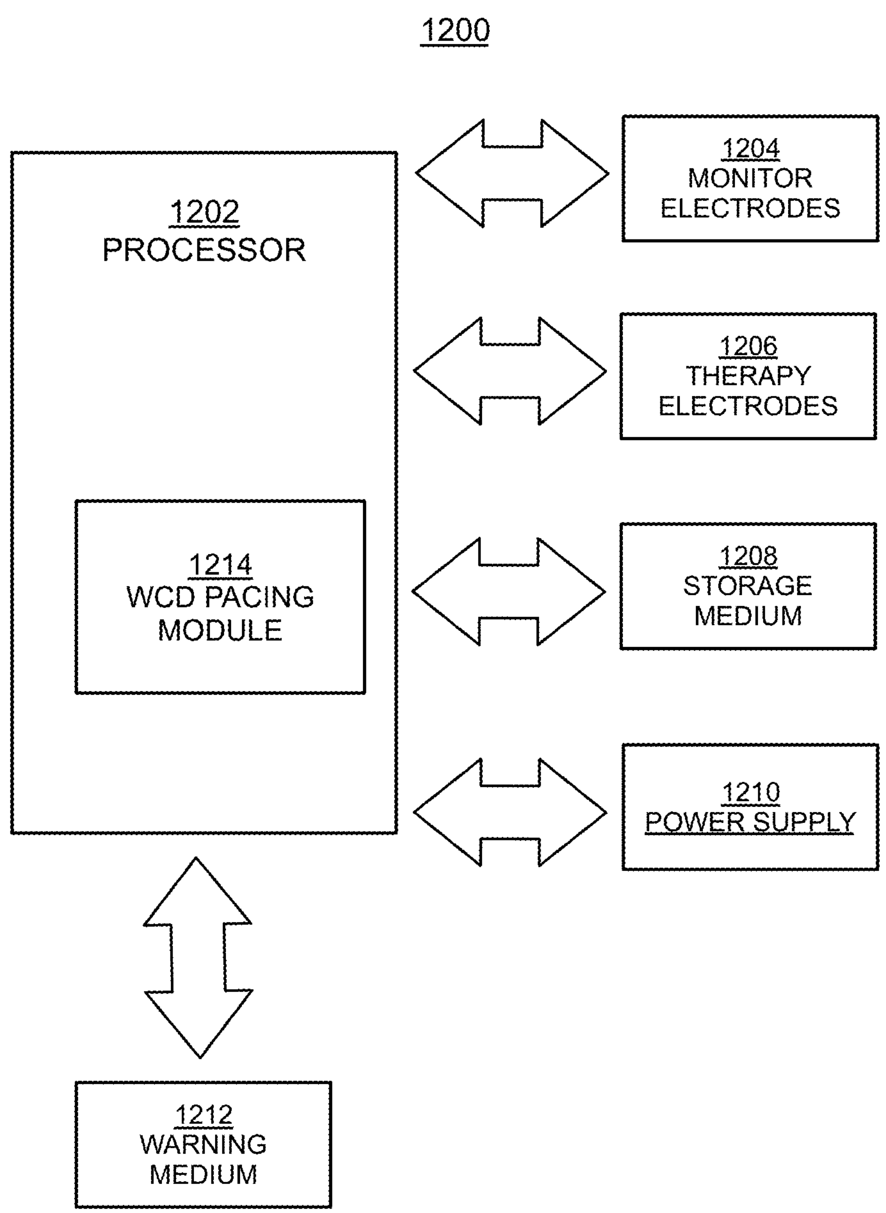
FIG. 12 illustrates a block diagram of a system for detecting and confirming cardiac pacing prior to pacing in accordance with various embodiments.

FIG. 12 illustrates a block diagram of a system for detecting and confirming cardiac pacing prior to pacing in accordance with various embodiments. In FIG. 12, a wearable cardioverter defibrillator (WCD) system 1200 may include a processor 1202, one or more monitor electrodes (hereon, monitor electrodes 1204), two therapy electrodes (hereon, therapy electrodes 1206), a storage medium 1208, and a power supply 1210. As shown, the monitor electrodes 1204, the therapy electrodes 1206, the storage medium 1208, and the power supply 1210 may all be communicatively coupled to the processor 1202 (i.e., under the control of the processor 1202). Additionally, the WCD system 1200 may include a warning medium 1212 communicatively coupled to the processor 1202, and the processor may include a WCD pacing module 1214 in accordance with one or more embodiments.

In FIG. 12, the monitor electrodes 1204 may be configured to receive electrocardiogram (ECG) signals. The WCD pacing module 1214 may be capable of determining if the received ECG signal meets a cardiac pacing criteria, where the cardiac pacing criteria may be stored in the storage medium 1208. Responsive to determining that the ECG signal meets a cardiac pacing criteria, the WCD pacing module 1214 may be capable of causing a warning to be communicated via the warning medium 1212 to indicate that cardiac pacing will be performed by the WCD. If no response or action is received by the WCD pacing module 1214, the WCD pacing module 1214 may be capable of providing electrical energy from the power supply 1210 as cardiac pacing pulses to the therapy electrodes 1206 as described above.

In the block diagram of FIG. 12, the warning medium 1212 may be a variety of warning mediums such as, but not limited to, visual and/or audio medium (e.g., light, user interface, speaker, etc.). The power supply 1210 may be a variety of power supplies such as, but not limited to, a battery, an alternating current (AC) outlet, a generator, and so forth. The monitor electrodes 1204 may include one or numerous electrodes, which may be of a variety of types to facilitate monitoring various physiological activities (e.g., ECG signal, respiration, $SPO_2$, etc.). The therapy electrodes 1206 may be a wide variety of therapy electrodes, which may be configured to facilitate providing electrical energy to pace and/or shock the heart of a person. Additionally, the monitor electrodes 1204 and/or the therapy electrodes 1206 may include mechanisms to provide conductive material (e.g., electrolyte gel) to an interface to improve conduction of pacing and/or defibrillation pulses to the person as described herein.

In FIG. 12, the processor 1202 may be a wide variety of processors to facilitate at least some of the functionality described herein such as, but not limited to, machine learning capable processors. Some of examples of machine learning capable processors may include processors available from Intel Corporation of Santa Clara, California (e.g., Nervana™ type processors), available from Nvidia Corporation of Santa Clara, California (e.g., Volta™ type processors), available from Apple Company of Cupertino, California (e.g., All Bionic™ type processors), available from Huawei Technologies Company of Shenzen, Guangdong, China (e.g., Kirin™ type processors), available from Advanced Micro Devices, Inc. of Sunnyvale, California (e.g., Radeon Instinct™ type processors), available from Samsung of Seoul, South Korea (e.g., Exynos™ type processors), and so forth. Accordingly, the claimed subject matter is not limited in this respect.

Figure 13:
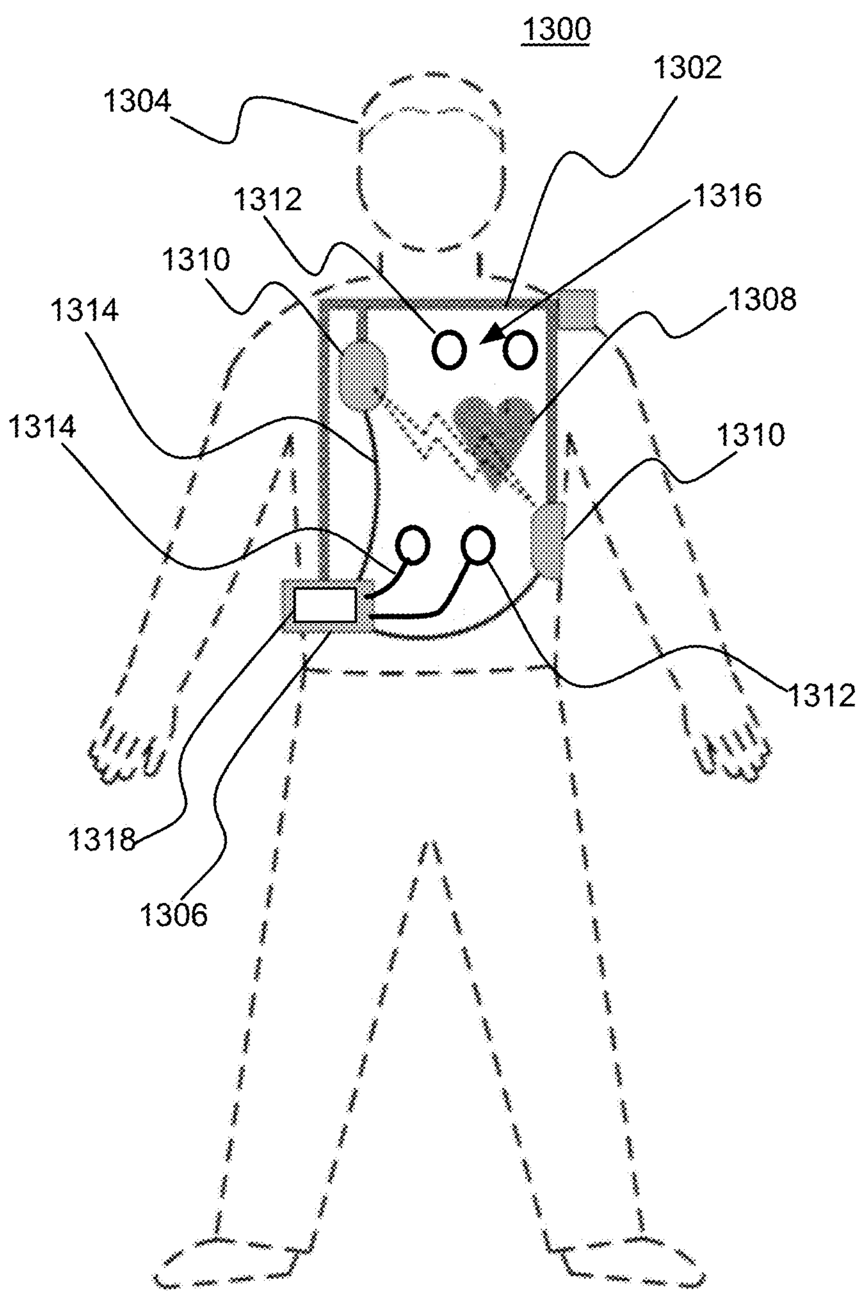
FIG. 13 illustrates an example of a medical device that may be utilized, in accordance with at least one or more example embodiments.

FIG. 13 illustrates an example of a medical device that may be utilized, in accordance with at least one or more example embodiments. In FIG. 13, a medical device may be a wearable medical device (WMD), which may be configured to facilitate monitoring and treatment of a person's heart such as, but not limited to, a wearable cardioverter defibrillator (WCD) 1300. The WCD 1300 may be included in or attached to a support structure 1302, which may be configured to be worn by a person 1304. The WCD 1300 may include various electronic components to facilitate the functionality of the WCD 1300 as a heart monitoring and defibrillator device including defibrillation and cardiac pacing functionality as described herein. The various electronic components may be illustrated as a WCD monitor 1306. The WCD 1300 may include two therapy electrodes configured to defibrillate a heart 1308 of the person 1304, defibrillator electrodes 1310, and a number of monitoring electrodes 1312 configured to detect and measure the person's electrical heart activity (e.g., electrocardiogram or ECG). As shown, the monitoring electrodes 1312 and the defibrillator electrodes 1310 may be located proximate to the heart 1308 and chest area 1316. The monitoring electrodes 1312 and the defibrillator electrodes 1310 may be communicatively coupled to the WCD monitor 1306 via a number of electrical leads 1314. Additionally, shown in FIG. 13, the WCD monitor 1306 may include a WCD pacing module 1318.

In FIG. 13, the support structure 1302 may be in the form of a garment configured to be worn by the person 1304. In some examples, the monitoring electrodes 1312, shown in FIG. 13, may be configured to be wirelessly coupled with the WCD monitor 1306.

As described herein, the WCD pacing module 1318 included in the WCD monitor 1306 may be configured to determine if received ECG signal meets one or more cardiac pacing criteria, where the ECG signal may be received via the monitoring electrodes 1312. The WCD pacing module 1318 may be configured to cause a warning to be communicated responsive to determining that the received ECG signal meets one or more cardiac pacing criteria. The warning may be configured to indicate that cardiac pacing will be performed by the WCD 1300. The warning may be visual and/or audio type and may be included in the support structure 1302. After the warning is provide, the WCD pacing module 1318 may be configured to cause the WCD monitor 1306 to provide electrical energy as cardiac pacing pulses to the defibrillator electrodes 1310 for cardiac pacing of the heart 1308 of the person 1304. In one example, the WCD pacing module 1318 may be capable of causing WCD monitor 1306 to provide cardiac pacing having alternating polarity between the defibrillator electrodes 1310. Additionally, the electrical energy may be provided from one or more components included in the WCD monitor 1306, such as for example, a dedicated battery for pacing pulses, a power supply used to power the WCD monitor 1306, a capacitor for storing electrical charge for defibrillation shocks, a charger for charging a the capacitor, etc.

As a result, the WCD 1300 may facilitate detecting and confirming one or more cardiac pacing criteria prior to cardiac pacing in accordance with various embodiments.

In FIG. 13, the support structure 1302 may be configured to support various components such as, but not limited to, the warning medium 1210, the power supply 1210, the storage medium 108, the processor 102, and any combination thereof. The components may be configured to facilitate the operation of the herein described functionality and disclosure.

In FIG. 13, the person 1304 may experience a heart related event (e.g., an arrhythmia of some kind). The received ECG signals from the one or more electrodes 1312 may indicate the onset of the heart related event, which may meet one or more cardiac pacing criteria. In response, the WCD pacing module 1318 may cause a warning to be communicated, where the warning may be configured to indicate that cardiac pacing will be performed by the WCD 1300. The WCD pacing module may cause the WCD monitor 1306 to provide electrical energy as cardiac pacing pulses to the therapy electrodes 1310 for cardiac pacing of the person 1304, namely, the heart 1308. Additionally, references may be made to FIG. 13 to facilitate various functionalities and configurations in accordance with various embodiments disclosed herein.

It should be appreciated after review of this disclosure that it is contemplated within the scope and spirit of the present disclosure that the claimed subject matter may include a wide variety of medical devices and healthcare devices. As described above, the WCD 1300 is only but one example of a medical device. Accordingly, the claimed subject matter is not limited in these respects.

Figure 14:
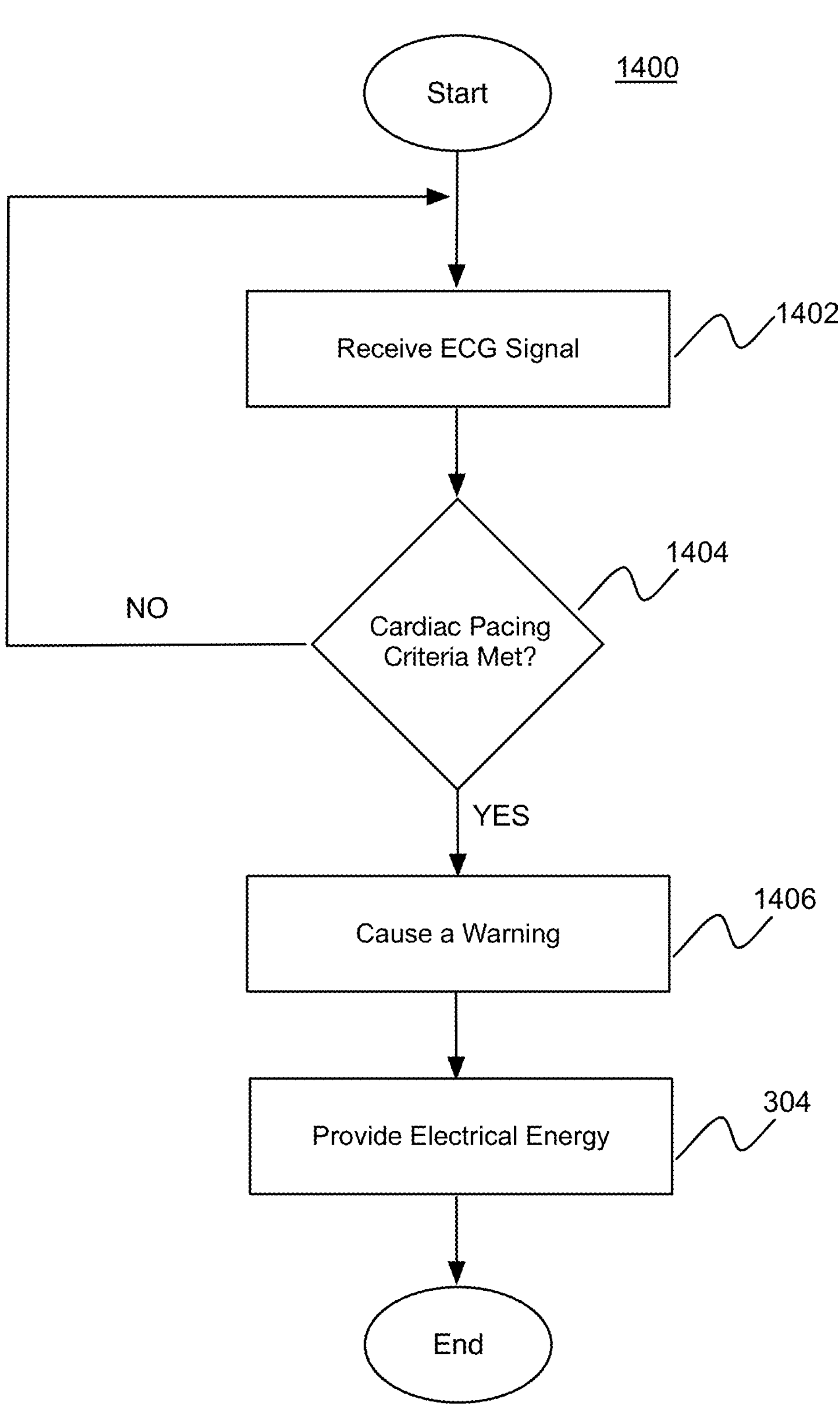
FIG. 14 illustrates an operational flow for determining pacing criteria and confirming prior to cardiac pacing by a medical device in accordance with various embodiments as described herein.

FIG. 14 illustrates an operational flow for determining one or more pacing criteria and confirming prior to cardiac pacing by a medical device in accordance with various embodiments as described herein. In some portions of the description, illustrative implementations of the method are described with reference to the elements depicted in FIGS. 12 and 13. However, the described embodiments are not limited to these depictions.

Additionally, FIG. 14 employs block diagrams to illustrate the example methods detailed therein. These block diagrams may set out various functional block or actions that may be described as processing steps, functional operations, events and/or acts, etc., and may be performed by hardware, software, and/or firmware. Numerous alternatives to the functional blocks detailed may be practiced in various implementations. For example, intervening actions not shown in the figures and/or additional actions not shown in the figures may be employed and/or some of the actions shown in one figure may be operated using techniques discussed with respect to another figure. Additionally, in some examples, the actions shown in these figures may be operated using parallel processing techniques. The above described, and other not described, rearrangements, substitutions, changes, modifications, etc., may be made without departing from the scope of the claimed subject matter.

In some examples, operational flow 1400 may be employed as part of medical device having cardiac pacing capabilities. Beginning at block 1402 ("Receive ECG Signal"), a wearable device system including a WMD (which may be a WCD in some embodiments), two therapy electrodes, one or more monitor electrodes, and a WCD pacing module, where the one or more monitor electrodes may be configured to receive electrocardiogram (ECG) signal. The ECG signal may be from an activity of a heart of a person.

Continuing from block 1402 to decision diamond 1404 ("Cardiac Pacing Criteria Met?"), the WCD pacing module may determine if one or more pacing criteria is met. For example, the WCD pacing module may determine if ECG signal indicates some form of cardiac event such as, but not limited to, a bradycardia event, an asystole event, a shockable event, and the like.

Responsive to determining that one or more cardiac pacing criteria is met, the WCD pacing module may cause the WCD to issue a warning to be communicated at block 1406 ("Cause a Warning"). The warning may be visual and/or audio as previously described.

Continuing from block 1406 to block 1408, the WCD may provide electrical energy as cardiac pacing pulses to the two therapy electrodes for cardiac pacing of the person.

In the decision diamond 1404, if one or more cardiac pacing criteria is not met, the WCD pacing module may continue to receive ECG signal from the monitor electrodes and continue to perform analysis of the ECG signal. For example, the WCD pacing module may determine that the received ECG signal may indicate a shockable event, and accordingly, may cause the WCD to defibrillate the heart (e.g., provide an electric shock for defibrillation).

As described herein, the type of healthcare device may include a wide variety of devices and form factors such as, but not limited to, an emergency medical device.

In general, the operational flow described with respect to FIG. 14 and elsewhere herein may be implemented as a computer program product, executable on any suitable computing system, or the like. For example, a computer program product for managing communication of information regarding a medical device may be provided. Example computer program products may be described with respect to FIG. 15 and elsewhere herein.

Figure 15:
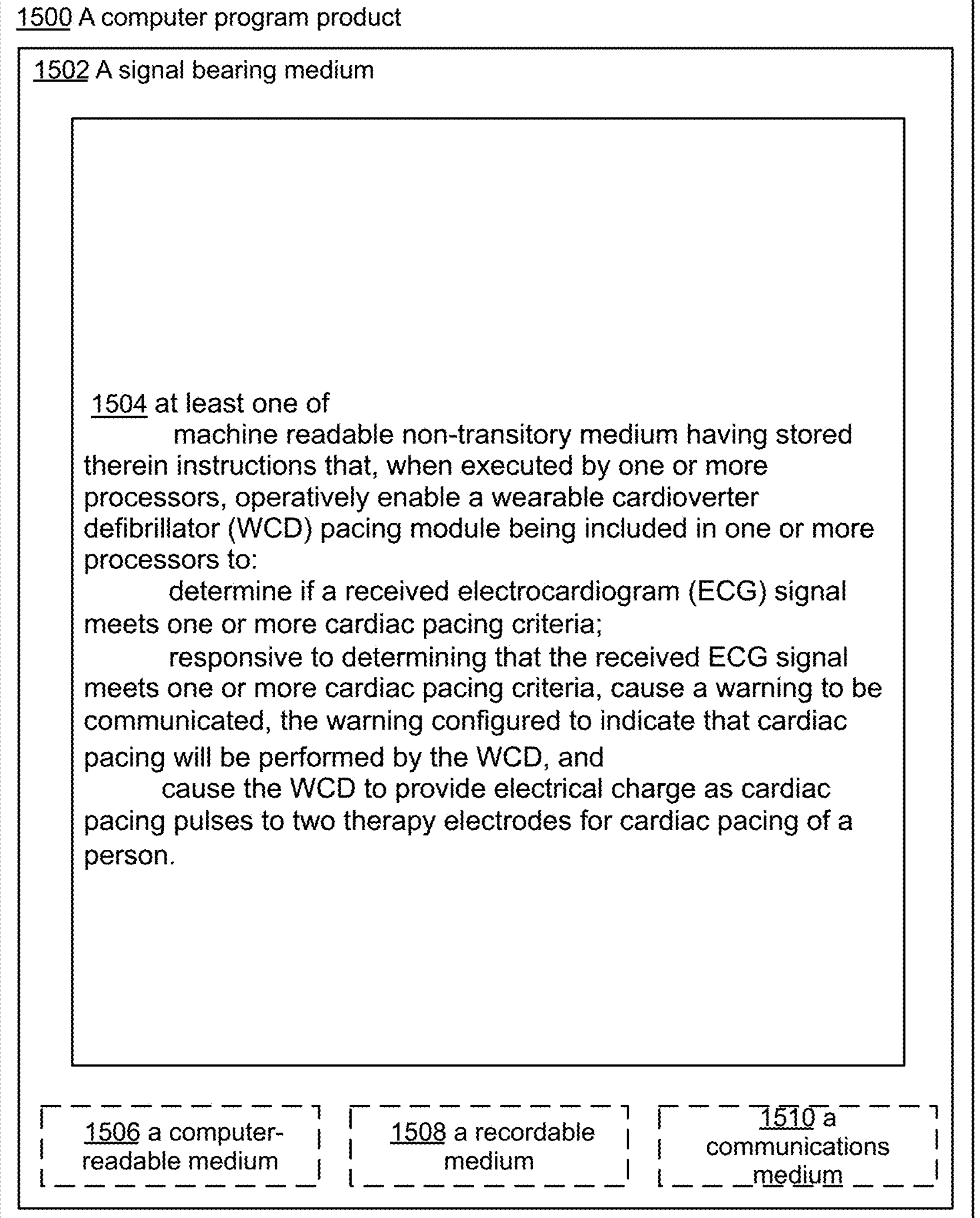
FIG. 15 illustrates an example computer program product, arranged in accordance with at least some embodiments described herein.

FIG. 15 illustrates an example computer program product 1500, arranged in accordance with at least some embodiments described herein. Computer program product 1500 may include machine readable non-transitory medium having stored therein instructions that, when executed, cause the machine to determining one or more pacing criteria and confirming prior to cardiac pacing by a medical device, according to the processes and methods discussed herein. Computer program product 1500 may include a signal bearing medium 1502. Signal bearing medium 1502 may include one or more machine-readable instructions 1504 which, when executed by one or more processors, may operatively enable a computing device to provide the functionality described herein. In various examples, the devices discussed herein may use some or all of the machine-readable instructions.

In some examples, the machine readable instructions 1504 may include an WCD pacing module configured to determine if a received ECG signal meets one or more cardiac pacing criteria, where the ECG signal may be received via one or more monitoring electrodes. In some examples, the machine readable medium 1504 may facilitate the WCD pacing module to, responsive to determining that the received ECG signal meets one or more cardiac pacing criteria, cause a warning to be communicated for example by the WCD. The warning is configured to indicate that cardiac pacing will be performed by the WCD. In some examples, the machine readable medium 1504 may facilitate the WCD pacing module to cause the WCD to provide electrical energy as cardiac pacing pulses to the two therapy electrodes for cardiac pacing of the person.

In some implementations, signal bearing medium 1502 may encompass a computer-readable medium 1506, such as, but not limited to, a hard disk drive, a Compact Disc (CD), a Digital Versatile Disk (DVD), a Universal Serial Bus (USB) drive, a digital tape, memory, etc. In some implementations, the signal bearing medium 1502 may encompass a recordable medium 1508, such as, but not limited to, memory, read/write (R/W) CDs, R/W DVDs, etc. In some implementations, the signal bearing medium 1502 may encompass a communications medium 1510, such as, but not limited to, a digital and/or an analog communication medium (e.g., a fiber optic cable, a waveguide, a wired communication link, a wireless communication link, etc.). In some examples, the signal bearing medium 1502 may encompass a machine readable non-transitory medium.

In general, the methods described with respect to FIG. 15 and elsewhere herein may be implemented in any suitable computing system. Example systems may be described with respect to FIG. 16 and elsewhere herein. In general, the system may be configured to facilitate a smart WCD pacing module for confirming cardiac pacing in accordance with various embodiments.

Figure 16:
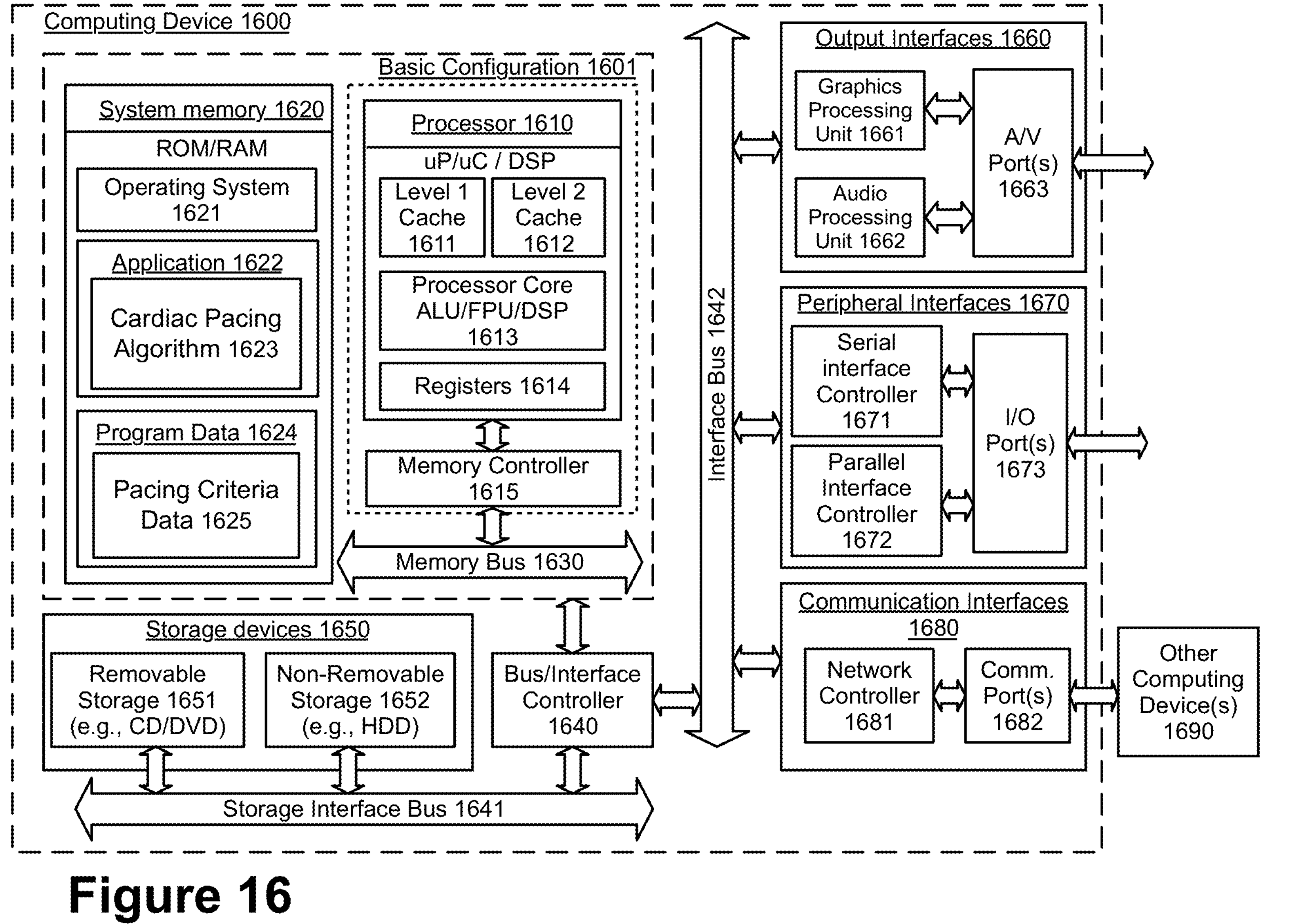
FIG. 16 is a block diagram illustrating an example computing device 1600, such as might be embodied by a person skilled in the art, which is arranged in accordance with at least some embodiments of the present disclosure.

FIG. 16 is a block diagram illustrating an example computing device 1600, such as might be embodied by a person skilled in the art, which is arranged in accordance with at least some embodiments of the present disclosure. In one example configuration, computing device 1600 may include one or more processors 1610 and system memory 1620. A memory bus 1630 may be used for communicating between the processor 1610 and the system memory 1620.

Depending on the desired configuration, processor 1610 may be of any type including but not limited to a microprocessor (μP), a microcontroller (μC), a digital signal processor (DSP), or any combination thereof. Processor 1610 may include one or more levels of caching, such as a level one cache 1611 and a level two cache 1612, a processor core 1613, and registers 1614. The processor core 1613 may include an arithmetic logic unit (ALU), a floating point unit (FPU), a digital signal processing core (DSP Core), or any combination thereof. A memory controller 1615 may also be used with the processor 1610, or in some implementations the memory controller 1615 may be an internal part of the processor 1610.

Depending on the desired configuration, the system memory 1620 may be of any type including but not limited to volatile memory (such as RAM), non-volatile memory (such as ROM, flash memory, etc.) or any combination thereof. System memory 1620 may include an operating system 1621, one or more applications 1622, and program data 1624. Application 1622 may include cardiac pacing algorithm 1623 that is arranged to perform the functions as described herein including the functional blocks and/or actions described. Program Data 1624 may include, among other information described, types of cardiac pacing criteria data 1625 for use with the cardiac pacing algorithm 1623. In some example embodiments, application 1622 may be arranged to operate with program data 1624 on an operating system 1621 such that implementations of WCD pacing module having determination and confirming capabilities may be provided as described herein. For example, apparatus described in the present disclosure may comprise all or a portion of computing device 1600 and be capable of performing all or a portion of application 1622 such that the WCD pacing module may determine if the received ECG signal meets one or more cardiac pacing criteria. Responsive to determining that the received ECG signal meets one or more cardiac pacing criteria, cause a warning to be communicated, where the warning may be configured to indicate that cardiac pacing will be performed by the WCD, and provide electrical energy as cardiac pacing pulses to the two therapy electrodes for cardiac pacing of the person as described herein. This described basic configuration is illustrated in FIG. 16 by those components within dashed line 1601.

Computing device 1600 may have additional features or functionality, and additional interfaces to facilitate communications between the basic configuration 1601 and any required devices and interfaces. For example, a bus/interface controller 1640 may be used to facilitate communications between the basic configuration 1601 and one or more data storage devices 1650 via a storage interface bus 1641. The data storage devices 1650 may be removable storage devices 1651, non-removable storage devices 1652, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer readable instructions, data structures, program modules, or other data.

System memory 1620, removable storage 1651 and non-removable storage 1652 are all examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 1600. Any such computer storage media may be part of device 1600.

Computing device 1600 may also include an interface bus 1642 for facilitating communication from various interface devices (e.g., output interfaces, peripheral interfaces, and communication interfaces) to the basic configuration 1601 via the bus/interface controller 1640. Example output interfaces 1660 may include a graphics processing unit 1661 and an audio processing unit 1662, which may be configured to communicate to various external devices such as a display or speakers via one or more A/V ports 1663. Example peripheral interfaces 1660 may include a serial interface controller 1671 or a parallel interface controller 1672, which may be configured to communicate with external devices such as input devices (e.g., keyboard, mouse, pen, voice input device, touch input device, etc.) or other peripheral devices (e.g., printer, scanner, etc.) via one or more I/O ports 1673. An example communication interface 1680 includes a network controller 1681, which may be arranged to facilitate communications with one or more other computing devices 1690 over a network communication via one or more communication ports 1682. A communication connection is one example of a communication media. Communication media may typically be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), infrared (IR) and other wireless media. The term computer readable media as used herein may include both storage media and communication media.

Computing device 1600 may be implemented as a portion of a small-form factor portable (or mobile) electronic device such as a cell phone, a personal data assistant (PDA), a personal media player device, a wireless web-watch device, a personal headset device, an application specific device, or a hybrid device that includes any of the above functions. Computing device 1600 may also be implemented as a personal computer including both laptop computer and non-laptop computer configurations. In addition, computing device 1600 may be implemented as part of a wireless base station or other wireless system or device.

What is claimed is:

1. A wearable cardioverter defibrillator (WCD) system, the WCD system comprising:

a WCD configured to be worn by a person and to provide defibrillation therapy responsive to an electrocardiogram (ECG) signal of the person received via at least two monitor electrodes being indicative of ventricular fibrillation; and a WCD pacing module configured to:

determine whether the received ECG signal meets one or more cardiac pacing criteria, responsive to determining that the received ECG signal meets the one or more cardiac pacing criteria, cause a warning to be communicated, the warning configured to indicate that cardiac pacing will be performed by the WCD, and cause the WCD to provide electrical charge as cardiac pacing pulses to at least two therapy electrodes for cardiac pacing of the person, wherein the cardiac pacing pulses are provided in a plurality of groups separated by at least one pause, the at least one pause having a duration greater than a period between successive cardiac pacing pulses within each of the plurality of groups to identify an intrinsic QRS complex in the received ECG signal, and wherein the WCD pacing module is further configured to cause the WCD to discontinue the cardiac pacing responsive to identification of the intrinsic QRS complex in the received ECG signal during the at least one pause.

2. The WCD system of claim 1, wherein the one or more cardiac pacing criteria comprise one or more bradycardia pacing criteria.

3. The WCD system of claim 1, wherein the one or more cardiac pacing criteria comprise one or more asystole pacing criteria.

4. The WCD system of claim 1, wherein the WCD pacing module is further configured to perform confirmation operations to confirm that the ECG signal meets the one or more cardiac pacing criteria, the confirmation operations comprising:

analyze a first portion of the received ECG signal, analyze a second portion of the received ECG signal, the second portion being subsequent to the first portion in time, and determine whether the second portion matches the first portion of the received ECG signal.

5. The WCD system of claim 1, wherein the WCD is configured to provide the electrical charge from a charger used to charge a capacitor of the WCD.

6. The WCD system of claim 1, wherein the WCD pacing module is further configured to detect an input to a user interface after the warning and in response, cause the WCD to not provide the cardiac pacing pulses.

7. The WCD system of claim 1, wherein the WCD pacing module is further configured to detect an indication of cardiopulmonary resuscitation (CPR) activity, and responsive to detection of the indication of CPR activity, terminate the cardiac pacing pulses to the at least two therapy electrodes.

8. The WCD system of claim 7, wherein the detection of CPR activity comprises determining a change in impedance between the at least two monitor electrodes.

9. The WCD system of claim 1, wherein the WCD pacing module is further configured to cause the WCD to provide the cardiac pacing pulses in an alternating polarity between the at least two therapy electrodes for the cardiac pacing of the person.

10. The WCD system of claim 1, wherein the cardiac pacing pulses comprise a cardiac pacing rate between 20 beats per minute (bpm) and 90 bpm.

11. The WCD system of claim 1, wherein the WCD is configured to provide the electrical charge using at least some electrical charge from a capacitor.

12. The WCD system of claim 1, wherein the WCD is configured to provide the electrical charge from a current source.

13. The WCD system of claim 1, wherein the one or more cardiac pacing criteria comprise a criterion based on a posture of the person, and wherein the WCD pacing module is further configured to determine the posture of the person using a sensor included in a support structure worn by the person.

14. The WCD system of claim 1, further configured to determine a proximity of a bystander, the determination being based on a signal from a proximity sensor included in a support structure worn by the person or in the WCD.

15. The WCD system of claim 1, further comprising:

a speaker configured to output the warning, wherein the WCD pacing module is further configured to cause the speaker to output the warning prior to providing the cardiac pacing pulses; and a user interface, wherein the WCD pacing module is further configured to receive an indication to not commence cardiac pacing at the user interface after the warning has been output and responsive to the received indication, not cause the WCD to provide the cardiac pacing pulses.

16. The WCD system of claim 1, wherein the plurality of groups and the at least one pause are periodic.

17. A wearable medical device (WMD) system, the WMD system comprising:

a WMD including:

a plurality of electrodes; and a user interface, wherein the WMD system is configured to perform operations comprising:

receive an electrocardiogram (ECG) signal via the plurality of electrodes, determine whether the received ECG signal meets one or more cardiac pacing criteria, responsive to determining that the received ECG signal meets the one or more cardiac pacing criteria, cause the WMD system to provide a pacing active warning, the pacing active warning being configured to indicate that cardiac pacing pulses are being provided to a person via the plurality of electrodes, wherein the cardiac pacing pulses are provided in a plurality of groups separated by at least one pause, the at least one pause having a duration greater than a period between successive cardiac pacing pulses within each of the plurality of groups to identify an intrinsic QRS complex in the received ECG signal; and receive an indication via the user interface to stop cardiac pacing and responsive to the received indication, cause the WMD to stop providing the cardiac pacing pulses, wherein the cardiac pacing is discontinued responsive to identification of the intrinsic QRS complex in the received ECG signal during the at least one pause.

18. The WMD system of claim 17, wherein the plurality of electrodes comprises a plurality of monitor electrodes and a plurality of therapy electrodes.

19. A wearable cardioverter defibrillator (WCD) system, the WCD system comprising:

a plurality of electrodes;

one or more processors communicatively coupled to the plurality of electrodes; and a user interface communicatively coupled to the one or more processors, wherein the one or more processors are configured to:

receive an electrocardiogram (ECG) signal via the plurality of electrodes, determine whether the received ECG signal meets one or more cardiac pacing criteria, responsive to determining that the received ECG signal meets the one or more cardiac pacing criteria, cause the WCD system to provide a pacing active warning, the pacing active warning being configured to indicate that cardiac pacing pulses are provided via the plurality of electrodes, wherein the cardiac pacing pulses are provided in a plurality of groups separated by at least one pause, the at least one pause having a duration greater than a period between successive cardiac pacing pulses within each of the plurality of groups to identify an intrinsic QRS complex in the received ECG signal; and receive an indication via the user interface to stop cardiac pacing and responsive to the received indication, cause the WCD system to stop providing the cardiac pacing pulses, wherein the cardiac pacing is discontinued responsive to identification of the intrinsic QRS complex in the received ECG signal during the at least one pause.

20. The WCD system of claim 19, wherein the one or more cardiac pacing criteria comprise one or more asystole pacing criteria.

* * * * *